(12) United States Patent
Wagner et al.

(10) Patent No.: US 10,898,709 B2
(45) Date of Patent: Jan. 26, 2021

(54) STIMULATION FOR TREATING SLEEP DISORDERED BREATHING

(71) Applicant: INSPIRE MEDICAL SYSTEMS, INC., Golden Valley, MN (US)

(72) Inventors: Darrell Wagner, Ham Lake, MN (US);
Quan Ni, Golden Valley, MN (US);
John Rondoni, Plymouth, MN (US);
David Dieken, Minneapolis, MN (US)

(73) Assignee: Inspire Medical Systems, Inc., Golden Valley, MN (US)

( * ) Notice: Subject to any disclaimer, the term of this patent is extended or adjusted under 35 U.S.C. 154(b) by 0 days.

(21) Appl. No.: 15/562,714

(22) PCT Filed: Mar. 16, 2016

(86) PCT No.: PCT/US2016/022611
§ 371 (c)(1),
(2) Date: Sep. 28, 2017

(87) PCT Pub. No.: WO2016/149344
PCT Pub. Date: Sep. 22, 2016

(65) Prior Publication Data
US 2018/0117316 A1 May 3, 2018

Related U.S. Application Data

(60) Provisional application No. 62/135,305, filed on Mar. 19, 2015.

(51) Int. Cl.
*A61N 1/00* (2006.01)
*A61N 1/36* (2006.01)
(Continued)

(52) U.S. Cl.
CPC .......... *A61N 1/3601* (2013.01); *A61B 5/0816* (2013.01); *A61B 5/0826* (2013.01);
(Continued)

(58) Field of Classification Search
CPC ... A61B 5/3601; A61B 5/0816; A61B 5/0826; A61B 5/113; A61B 5/4818;
(Continued)

(56) References Cited

U.S. PATENT DOCUMENTS

| 4,379,462 A | 4/1983 | Borkan et al. |
| 4,567,892 A | 2/1986 | Plicchi et al. |

(Continued)

FOREIGN PATENT DOCUMENTS

| CN | 102548610 A | 7/2012 |
| JP | H11514557 | 12/1999 |

(Continued)

OTHER PUBLICATIONS

Eisele Article—David W. Eisele, MD et al., "Tongue neuromuscular and direct hypoglossal nerve stimulation for obstructive sleep apnea," Otolaryngologic Clinics of North America, Otolayngol Clin N Am 36 (2003) 501-510 (10 pages).
(Continued)

*Primary Examiner* — Carl H Layno
*Assistant Examiner* — Michael J Lau
(74) *Attorney, Agent, or Firm* — Dicke, Billig & Czaja, PLLC

(57) ABSTRACT

A device for treating sleep disordered breathing includes a stimulation element to stimulate an airway-patency-related nerve.

15 Claims, 13 Drawing Sheets

(51) Int. Cl.
*A61B 5/08* (2006.01)
*A61B 5/00* (2006.01)
*A61B 5/113* (2006.01)
*G06F 19/00* (2018.01)
*A61B 5/0205* (2006.01)

(52) U.S. Cl.
CPC ............ *A61B 5/113* (2013.01); *A61B 5/4818* (2013.01); *A61B 5/4848* (2013.01); *A61B 5/686* (2013.01); *A61N 1/3611* (2013.01); *A61B 5/0205* (2013.01); *A61N 1/3614* (2017.08); *A61N 1/36146* (2013.01); *A61N 1/36171* (2013.01); *G06F 19/3481* (2013.01)

(58) Field of Classification Search
CPC ... A61B 5/4848; A61B 5/686; A61B 1/36135; A61N 1/3611; A61N 1/36135; A61N 1/36146; A61N 1/36171; G06F 19/3481
USPC .............................................. 607/42, 72, 73
See application file for complete search history.

(56) References Cited

U.S. PATENT DOCUMENTS

| | | |
|---|---|---|
| 4,630,614 A | 12/1986 | Atlas |
| 4,813,431 A | 3/1989 | Brown |
| 4,830,008 A | 5/1989 | Meer |
| 5,123,425 A | 6/1992 | Shannon, Jr. et al. |
| 5,133,354 A | 7/1992 | Kallok |
| 5,134,995 A | 8/1992 | Gruenke et al. |
| 5,148,802 A | 9/1992 | Sanders et al. |
| 5,158,080 A | 10/1992 | Kallok |
| 5,167,229 A | 12/1992 | Peckham et al. |
| 5,174,287 A | 12/1992 | Kallok et al. |
| 5,178,156 A | 1/1993 | Takishima et al. |
| 5,190,053 A | 3/1993 | Meer |
| 5,203,343 A | 4/1993 | Axe et al. |
| 5,211,173 A | 5/1993 | Kallok et al. |
| 5,215,082 A | 6/1993 | Kallok et al. |
| 5,233,983 A | 8/1993 | Markowitz |
| 5,239,995 A | 8/1993 | Estes et al. |
| 5,245,995 A | 9/1993 | Sullivan et al. |
| 5,265,624 A | 11/1993 | Bowman |
| 5,281,219 A | 1/1994 | Kallok |
| 5,300,094 A | 4/1994 | Kallok et al. |
| 5,335,657 A | 8/1994 | Terry, Jr. et al. |
| 5,344,438 A | 9/1994 | Testerman et al. |
| 5,351,394 A | 10/1994 | Weinberg |
| 5,385,144 A | 1/1995 | Yamanishi et al. |
| 5,388,578 A | 2/1995 | Yomtov et al. |
| 5,398,682 A | 3/1995 | Lynn |
| 5,458,137 A | 10/1995 | Axe et al. |
| 5,483,969 A | 1/1996 | Testerman et al. |
| 5,485,851 A | 1/1996 | Erickson |
| 5,522,862 A | 6/1996 | Testerman et al. |
| 5,524,632 A | 6/1996 | Stein et al. |
| 5,540,731 A | 7/1996 | Testerman |
| 5,540,732 A | 7/1996 | Testerman |
| 5,540,733 A | 7/1996 | Testerman et al. |
| 5,540,734 A | 7/1996 | Zabara |
| 5,546,952 A | 8/1996 | Erickson |
| 5,549,655 A | 8/1996 | Erickson |
| 5,588,439 A | 12/1996 | Hollub |
| 5,591,216 A | 1/1997 | Testerman et al. |
| 5,605,151 A | 2/1997 | Lynn |
| 5,645,053 A | 7/1997 | Remmers et al. |
| 5,671,733 A | 9/1997 | Raviv et al. |
| 5,797,852 A | 8/1998 | Karakasoglu et al. |
| 5,823,187 A | 10/1998 | Estes et al. |
| 5,843,135 A | 12/1998 | Weijand et al. |
| 5,895,360 A | 4/1999 | Christopherson et al. |
| 5,904,141 A | 5/1999 | Estes et al. |
| 5,919,221 A | 7/1999 | Miesel |
| 5,944,680 A * | 8/1999 | Christopherson ........ A61B 5/03 128/897 |
| 5,999,846 A | 12/1999 | Pardey et al. |
| 6,015,389 A | 1/2000 | Brown |
| 6,021,352 A | 2/2000 | Christopherson et al. |
| 6,025,624 A | 2/2000 | Figura |
| 6,041,780 A | 3/2000 | Richard et al. |
| 6,099,479 A | 8/2000 | Christopherson et al. |
| 6,120,441 A | 9/2000 | Griebel |
| 6,125,290 A | 9/2000 | Miesel |
| 6,125,291 A | 9/2000 | Miesel et al. |
| 6,126,611 A | 10/2000 | Bourgeouis et al. |
| 6,132,384 A | 10/2000 | Christopherson et al. |
| 6,134,459 A | 10/2000 | Roberts et al. |
| 6,144,866 A | 11/2000 | Miesel et al. |
| 6,175,767 B1 | 1/2001 | Doyle, Sr. |
| 6,181,961 B1 | 1/2001 | Prass |
| 6,198,952 B1 | 3/2001 | Miesel |
| 6,223,064 B1 | 4/2001 | Lynn et al. |
| 6,240,316 B1 | 5/2001 | Richmond et al. |
| 6,248,080 B1 | 6/2001 | Miesel et al. |
| 6,249,703 B1 | 6/2001 | Stanton et al. |
| 6,251,126 B1 | 6/2001 | Ottenhoff et al. |
| 6,269,269 B1 | 7/2001 | Ottenhoff et al. |
| 6,307,481 B1 | 10/2001 | Lehrman et al. |
| 6,309,350 B1 | 10/2001 | Van Tassel et al. |
| 6,314,324 B1 | 11/2001 | Lattner et al. |
| 6,342,039 B1 | 1/2002 | Lynn et al. |
| 6,345,202 B2 | 2/2002 | Richmond et al. |
| 6,361,494 B1 | 3/2002 | Lindenthaler |
| 6,393,325 B1 | 5/2002 | Mann et al. |
| 6,449,507 B1 | 9/2002 | Hill et al. |
| 6,450,957 B1 | 9/2002 | Yoshimi et al. |
| 6,456,866 B1 | 9/2002 | Tyler et al. |
| 6,509,164 B1 | 1/2003 | Guirguis |
| 6,522,928 B2 | 2/2003 | Whitehurst et al. |
| 6,532,388 B1 | 3/2003 | Hill et al. |
| 6,572,543 B1 | 6/2003 | Christopherson et al. |
| 6,574,507 B1 | 6/2003 | Bonnet |
| 6,587,725 B1 | 7/2003 | Durand et al. |
| 6,609,016 B1 | 8/2003 | Lynn |
| 6,609,032 B1 | 8/2003 | Woods et al. |
| 6,629,527 B1 | 10/2003 | Estes et al. |
| 6,641,542 B2 | 11/2003 | Cho et al. |
| 6,645,143 B2 | 11/2003 | Van Tassel et al. |
| 6,647,289 B2 | 11/2003 | Prutchi |
| 6,651,652 B1 | 11/2003 | Ward |
| 6,654,634 B1 | 11/2003 | Prass |
| 6,665,560 B2 | 12/2003 | Becker et al. |
| 6,666,830 B1 | 12/2003 | Lehrman et al. |
| 6,689,068 B2 | 2/2004 | Hale et al. |
| 6,703,939 B2 | 3/2004 | Lehrman et al. |
| 6,718,208 B2 | 4/2004 | Hill et al. |
| 6,719,708 B1 | 4/2004 | Jansen |
| 6,731,976 B2 | 5/2004 | Penn et al. |
| 6,731,984 B2 | 5/2004 | Cho et al. |
| 6,735,471 B2 | 5/2004 | Hill et al. |
| 6,752,765 B1 | 6/2004 | Jensen et al. |
| 6,770,022 B2 | 8/2004 | Mechlenburg et al. |
| 6,773,404 B2 | 8/2004 | Poezevera et al. |
| 6,805,667 B2 | 10/2004 | Christopherson et al. |
| 6,811,538 B2 | 11/2004 | Westbrook et al. |
| 6,842,647 B1 | 1/2005 | Griffith et al. |
| 6,881,192 B1 | 4/2005 | Park |
| 6,890,306 B2 | 5/2005 | Poezevera |
| 6,893,405 B2 | 5/2005 | Kumar et al. |
| 6,904,320 B2 | 6/2005 | Park et al. |
| 6,907,293 B2 | 6/2005 | Grill et al. |
| 6,928,324 B2 | 8/2005 | Park et al. |
| 6,935,335 B1 | 8/2005 | Lehrman et al. |
| 6,936,011 B2 | 8/2005 | Sheldon |
| 6,964,641 B2 | 11/2005 | Cho et al. |
| 6,978,171 B2 | 12/2005 | Goetz et al. |
| 6,988,498 B2 | 1/2006 | Berthon-Jones et al. |
| 7,025,730 B2 | 4/2006 | Cho et al. |
| 7,041,049 B1 | 5/2006 | Raniere |
| 7,054,692 B1 | 5/2006 | Whitehurst et al. |
| 7,077,810 B2 | 7/2006 | Lange et al. |
| 7,081,095 B2 | 7/2006 | Lynn et al. |
| 7,082,331 B1 | 7/2006 | Park et al. |
| 7,082,336 B2 | 7/2006 | Ransbury et al. |

(56) References Cited

U.S. PATENT DOCUMENTS

| | | |
|---|---|---|
| 7,087,053 B2 | 8/2006 | Vanney |
| 7,117,036 B2 | 10/2006 | Florio |
| 7,128,717 B1 | 10/2006 | Thach et al. |
| 7,145,461 B2 | 12/2006 | Lehrman et al. |
| 7,149,573 B2 | 12/2006 | Wang |
| 7,155,278 B2 | 12/2006 | King et al. |
| 7,160,252 B2 | 1/2007 | Cho et al. |
| 7,160,255 B2 | 1/2007 | Saadat |
| 7,167,743 B2 | 1/2007 | Heruth et al. |
| 7,174,215 B2 | 2/2007 | Bradley |
| 7,186,220 B2 | 3/2007 | Stahmann et al. |
| 7,187,978 B2 | 3/2007 | Malek et al. |
| 7,189,204 B2 | 3/2007 | Ni et al. |
| 7,195,594 B2 | 3/2007 | Eigler et al. |
| 7,200,440 B2 | 4/2007 | Kim et al. |
| 7,206,635 B2 | 4/2007 | Cho et al. |
| 7,212,862 B2 | 5/2007 | Park et al. |
| 7,214,197 B2 | 5/2007 | Prass |
| 7,252,640 B2 | 8/2007 | Ni et al. |
| 7,269,457 B2 | 9/2007 | Shafer et al. |
| 7,269,459 B1 | 9/2007 | Koh |
| 7,277,749 B2 | 10/2007 | Gordon et al. |
| 7,330,760 B2 | 2/2008 | Heruth et al. |
| 7,336,996 B2 | 2/2008 | Hartley et al. |
| 7,340,302 B1 * | 3/2008 | Falkenberg ........... A61N 1/3611 607/9 |
| 7,351,208 B2 | 4/2008 | Brodnick et al. |
| 7,366,572 B2 | 4/2008 | Heruth et al. |
| 7,371,220 B1 | 5/2008 | Koh et al. |
| 7,387,608 B2 | 6/2008 | Dunlop et al. |
| 7,395,113 B2 | 7/2008 | Heruth et al. |
| 7,396,333 B2 | 7/2008 | Stahmann et al. |
| 7,398,115 B2 | 7/2008 | Lynn |
| 7,422,015 B2 | 9/2008 | Delisle et al. |
| 7,438,686 B2 | 10/2008 | Cho et al. |
| 7,447,545 B2 | 11/2008 | Heruth et al. |
| 7,454,250 B1 | 11/2008 | Bjorling et al. |
| 7,453,928 B2 | 12/2008 | Lee et al. |
| 7,468,040 B2 | 12/2008 | Hartley et al. |
| 7,469,697 B2 | 12/2008 | Lee et al. |
| 7,473,227 B2 | 1/2009 | Hsu et al. |
| 7,491,181 B2 | 2/2009 | Heruth et al. |
| 7,510,531 B2 | 3/2009 | Lee et al. |
| 7,526,341 B2 | 4/2009 | Goetz et al. |
| 7,542,803 B2 | 6/2009 | Heruth et al. |
| 7,572,225 B2 | 8/2009 | Stahmann et al. |
| 7,590,455 B2 | 9/2009 | Heruth et al. |
| 7,591,265 B2 | 9/2009 | Lee et al. |
| 7,596,413 B2 | 9/2009 | Libbus et al. |
| 7,603,170 B2 | 10/2009 | Hatlestad et al. |
| 7,610,094 B2 | 10/2009 | Stahmann et al. |
| 7,634,315 B2 | 12/2009 | Cholette |
| 7,644,714 B2 | 1/2010 | Atkinson et al. |
| 7,662,105 B2 | 2/2010 | Hatlestad |
| 7,672,728 B2 | 3/2010 | Libbus et al. |
| 7,678,061 B2 | 3/2010 | Lee et al. |
| 7,680,538 B2 | 3/2010 | Durand et al. |
| 7,702,385 B2 | 4/2010 | Moffitt et al. |
| 7,717,848 B2 | 5/2010 | Heruth et al. |
| 7,720,541 B2 | 5/2010 | Stahmann et al. |
| 7,725,195 B2 | 5/2010 | Lima et al. |
| 7,734,340 B2 | 6/2010 | De Ridder |
| 7,734,350 B2 | 6/2010 | Dubnov et al. |
| 7,742,819 B2 | 6/2010 | Moffitt |
| 7,747,323 B2 | 6/2010 | Libbus et al. |
| 7,751,880 B1 | 7/2010 | Cholette |
| 7,775,993 B2 | 8/2010 | Heruth et al. |
| 7,783,353 B2 | 8/2010 | Libbus et al. |
| 7,792,583 B2 | 9/2010 | Miesel et al. |
| 7,809,442 B2 * | 10/2010 | Bolea ................... A61N 1/0558 607/42 |
| 7,818,063 B2 | 10/2010 | Wallace et al. |
| 7,853,322 B2 | 12/2010 | Bourget et al. |
| 7,881,798 B2 | 2/2011 | Miesel et al. |
| 7,908,013 B2 | 3/2011 | Miesel et al. |
| 7,917,230 B2 | 3/2011 | Bly |
| 7,942,822 B1 | 5/2011 | Koh |
| 7,957,797 B2 | 6/2011 | Bourget et al. |
| 7,957,809 B2 | 6/2011 | Bourget et al. |
| 7,979,128 B2 | 7/2011 | Tehrani et al. |
| 8,016,776 B2 | 9/2011 | Bourget et al. |
| 8,021,299 B2 | 9/2011 | Miesel et al. |
| 8,150,531 B2 | 4/2012 | Skelton |
| 8,160,711 B2 | 4/2012 | Tehrani et al. |
| 8,160,712 B1 | 4/2012 | Freed |
| 8,175,720 B2 | 5/2012 | Skelton et al. |
| 8,233,987 B2 * | 7/2012 | Gelfand ............. A61N 1/36171 607/42 |
| 8,265,759 B2 * | 9/2012 | Tehrani ................ A61N 1/3627 607/42 |
| 8,280,513 B2 * | 10/2012 | Tehrani ................ A61N 1/3601 607/42 |
| 8,718,776 B2 | 5/2014 | Mashiach et al. |
| 8,781,587 B2 | 7/2014 | Alt et al. |
| 9,895,540 B2 | 2/2018 | Mashiach |
| 2001/0010010 A1 | 7/2001 | Richmond et al. |
| 2002/0010495 A1 | 1/2002 | Freed et al. |
| 2002/0049479 A1 | 4/2002 | Pitts |
| 2002/0156507 A1 | 10/2002 | Lindenthaler |
| 2003/0093128 A1 | 5/2003 | Freed et al. |
| 2003/0114905 A1 | 6/2003 | Kuzma |
| 2003/0224895 A1 | 6/2003 | Gordon et al. |
| 2003/0163059 A1 | 8/2003 | Poezevera et al. |
| 2003/0195571 A1 | 10/2003 | Burnes et al. |
| 2003/0216789 A1 | 11/2003 | Deem et al. |
| 2004/0015204 A1 | 1/2004 | Whitehurst et al. |
| 2004/0073272 A1 | 4/2004 | Knudson et al. |
| 2004/0111139 A1 | 6/2004 | McCreery |
| 2004/0215288 A1 | 10/2004 | Lee et al. |
| 2004/0230278 A1 | 11/2004 | Dahl et al. |
| 2004/0254612 A1 | 12/2004 | Ezra |
| 2005/0004628 A1 | 1/2005 | Goetz et al. |
| 2005/0010265 A1 | 1/2005 | Baru Fassio et al. |
| 2005/0042589 A1 | 2/2005 | Hatlestad et al. |
| 2005/0043765 A1 | 2/2005 | Williams et al. |
| 2005/0043772 A1 | 2/2005 | Stahmann et al. |
| 2005/0074741 A1 | 4/2005 | Lee et al. |
| 2005/0076908 A1 | 4/2005 | Lee et al. |
| 2005/0080348 A1 | 4/2005 | Stahmann et al. |
| 2005/0080461 A1 | 4/2005 | Stahmann et al. |
| 2005/0081847 A1 | 4/2005 | Lee et al. |
| 2005/0085865 A1 | 4/2005 | Tehrani |
| 2005/0085866 A1 | 4/2005 | Tehrani |
| 2005/0085868 A1 | 4/2005 | Tehrani et al. |
| 2005/0085869 A1 | 4/2005 | Tehrani et al. |
| 2005/0085874 A1 | 4/2005 | Davis et al. |
| 2005/0101833 A1 | 5/2005 | Hsu et al. |
| 2005/0113710 A1 | 5/2005 | Stahmann et al. |
| 2005/0115561 A1 | 6/2005 | Stahmann et al. |
| 2005/0145246 A1 | 7/2005 | Hartley et al. |
| 2005/0148897 A1 | 7/2005 | Cho et al. |
| 2005/0165457 A1 | 7/2005 | Benser et al. |
| 2005/0182457 A1 | 8/2005 | Thrope et al. |
| 2005/0209513 A1 | 9/2005 | Heruth et al. |
| 2005/0209643 A1 | 9/2005 | Heruth et al. |
| 2005/0222503 A1 | 10/2005 | Dunlop et al. |
| 2005/0234523 A1 | 10/2005 | Levin et al. |
| 2005/0251216 A1 | 11/2005 | Hill et al. |
| 2005/0261747 A1 | 11/2005 | Schuler et al. |
| 2005/0267380 A1 | 12/2005 | Poezevera |
| 2005/0277844 A1 | 12/2005 | Strother et al. |
| 2005/0277999 A1 | 12/2005 | Strother et al. |
| 2005/0278000 A1 | 12/2005 | Strother et al. |
| 2006/0052836 A1 | 3/2006 | Kim et al. |
| 2006/0058852 A1 | 3/2006 | Koh et al. |
| 2006/0064029 A1 | 3/2006 | Arad (Abboud) |
| 2006/0079802 A1 | 4/2006 | Jensen et al. |
| 2006/0095088 A1 | 5/2006 | De Ridder |
| 2006/0103407 A1 | 5/2006 | Kakizawa et al. |
| 2006/0135886 A1 | 6/2006 | Lippert et al. |
| 2006/0155341 A1 | 7/2006 | Tehrani et al. |
| 2006/0167523 A1 * | 7/2006 | Tehrani ................ A61N 1/3601 607/42 |
| 2006/0142815 A1 | 9/2006 | Tehrani et al. |

(56) References Cited

U.S. PATENT DOCUMENTS

| | | |
|---|---|---|
| 2006/0212096 A1 | 9/2006 | Stevenson |
| 2006/0224209 A1 | 10/2006 | Meyer |
| 2006/0241708 A1 | 10/2006 | Boute |
| 2006/0247729 A1* | 11/2006 | Tehrani ................ A61N 1/3601 607/42 |
| 2006/0259079 A1 | 11/2006 | King |
| 2006/0264777 A1 | 11/2006 | Drew |
| 2006/0266369 A1 | 11/2006 | Atkinson et al. |
| 2006/0271137 A1 | 11/2006 | Stanton-Hicks |
| 2006/0276701 A1 | 12/2006 | Ray |
| 2006/0293720 A1 | 12/2006 | DiLorenzo |
| 2006/0293723 A1 | 12/2006 | Whitehurst et al. |
| 2007/0021785 A1 | 1/2007 | Inman et al. |
| 2007/0027482 A1 | 2/2007 | Parnis et al. |
| 2007/0038265 A1 | 2/2007 | Tcheng et al. |
| 2007/0150022 A1 | 6/2007 | Ujhazy et al. |
| 2007/0233204 A1 | 10/2007 | Lima et al. |
| 2007/0255379 A1 | 11/2007 | Williams et al. |
| 2008/0009685 A1 | 1/2008 | Kim et al. |
| 2008/0039904 A1 | 2/2008 | Bulkes et al. |
| 2008/0046055 A1 | 2/2008 | Durand et al. |
| 2008/0064977 A1 | 3/2008 | Kelleher et al. |
| 2008/0103545 A1 | 5/2008 | Bolea et al. |
| 2008/0103570 A1 | 5/2008 | Gerber |
| 2008/0109046 A1 | 5/2008 | Lima et al. |
| 2008/0109048 A1 | 5/2008 | Moffitt |
| 2008/0132802 A1 | 6/2008 | Ni et al. |
| 2008/0154330 A1* | 6/2008 | Tehrani ................ A61N 1/3601 607/42 |
| 2008/0161878 A1* | 7/2008 | Tehrani ................ A61N 1/3601 607/42 |
| 2008/0294060 A1 | 11/2008 | Haro et al. |
| 2009/0024047 A1 | 1/2009 | Shipley et al. |
| 2009/0062882 A1* | 3/2009 | Zhang ................ A61N 1/3601 607/42 |
| 2009/0112116 A1 | 4/2009 | Lee et al. |
| 2009/0118787 A1 | 5/2009 | Moffitt et al. |
| 2009/0216293 A1 | 8/2009 | Sasaki et al. |
| 2009/0234427 A1 | 9/2009 | Chinn et al. |
| 2009/0287279 A1 | 11/2009 | Parramon et al. |
| 2009/0308395 A1 | 12/2009 | Lee et al. |
| 2009/0326408 A1 | 12/2009 | Moon |
| 2010/0010566 A1 | 1/2010 | Thacker et al. |
| 2010/0016749 A1 | 1/2010 | Atsma et al. |
| 2010/0094379 A1 | 4/2010 | Meadows |
| 2010/0125310 A1 | 5/2010 | Wilson et al. |
| 2010/0125314 A1 | 5/2010 | Bradley et al. |
| 2010/0125315 A1 | 5/2010 | Parramon et al. |
| 2010/0137931 A1 | 6/2010 | Hopper et al. |
| 2010/0152553 A1 | 6/2010 | Ujhazy et al. |
| 2010/0174341 A1* | 7/2010 | Bolea ................ A61N 1/0556 607/42 |
| 2010/0198103 A1 | 8/2010 | Meadows et al. |
| 2010/0198289 A1* | 8/2010 | Kameli ................ G06F 19/3481 607/14 |
| 2010/0228133 A1 | 9/2010 | Averina et al. |
| 2010/0228310 A1 | 9/2010 | Shuros et al. |
| 2010/0228317 A1 | 9/2010 | Libbus et al. |
| 2010/0241195 A1 | 9/2010 | Meadows et al. |
| 2010/0262210 A1 | 10/2010 | Parramon et al. |
| 2011/0060380 A1 | 3/2011 | Gelfand et al. |
| 2011/0093032 A1* | 4/2011 | Boggs, II ............ A61N 1/3611 607/42 |
| 2011/0093036 A1 | 4/2011 | Mashiach |
| 2011/0112601 A1 | 5/2011 | Meadows et al. |
| 2011/0152706 A1 | 6/2011 | Christopherson et al. |
| 2011/0152965 A1 | 6/2011 | Mashiach et al. |
| 2011/0160794 A1 | 6/2011 | Bolea et al. |
| 2011/0172733 A1 | 7/2011 | Lima et al. |
| 2011/0264164 A1 | 10/2011 | Christopherson et al. |
| 2011/0288609 A1* | 11/2011 | Tehrani .............. A61N 1/36031 607/42 |
| 2012/0192874 A1* | 8/2012 | Bolea ................ A61N 1/3601 128/848 |
| 2012/0253249 A1* | 10/2012 | Wilson ................ A61N 1/3611 601/154 |
| 2012/0290036 A1* | 11/2012 | Karamanoglu ........ A61B 5/686 607/42 |
| 2013/0253627 A1 | 9/2013 | Meadows et al. |
| 2014/0135868 A1* | 5/2014 | Bashyam ............. A61N 1/3601 607/42 |
| 2014/0228905 A1* | 8/2014 | Bolea ........................ A61F 5/56 607/42 |
| 2014/0364919 A1* | 12/2014 | Doan ................ A61N 1/36164 607/46 |
| 2015/0039045 A1 | 2/2015 | Ni et al. |
| 2015/0328451 A1* | 11/2015 | Kobayashi ........... A61N 1/0492 607/42 |
| 2016/0022204 A1* | 1/2016 | Mostov ................ A61B 5/0002 600/301 |
| 2016/0193468 A1 | 7/2016 | Rondoni et al. |
| 2016/0354602 A1 | 12/2016 | Keenan |
| 2016/0354603 A1 | 12/2016 | Keenan |
| 2016/0354608 A1* | 12/2016 | Keenan ................ A61N 1/3611 |
| 2017/0368337 A1 | 12/2017 | Steier |

FOREIGN PATENT DOCUMENTS

| | | | |
|---|---|---|---|
| JP | 4960704 B2 | 8/2008 | |
| JP | 2010502276 | 1/2010 | |
| JP | 2011520526 | 7/2011 | |
| JP | 2013509943 | 3/2013 | |
| JP | 5636129 B2 | 12/2015 | |
| WO | 199750049 | 12/1997 | |
| WO | WO-9750049 A1 * | 12/1997 | ............. A61B 5/03 |
| WO | WO199749455 | 12/1997 | |
| WO | 2006047264 | 5/2006 | |
| WO | 2006057734 | 6/2006 | |
| WO | 2006102591 | 9/2006 | |
| WO | 2007068284 | 6/2007 | |
| WO | 2008048471 | 4/2008 | |
| WO | 2009048580 | 4/2009 | |
| WO | 2009048581 | 4/2009 | |
| WO | 2009135138 | 11/2009 | |
| WO | 2009135140 | 11/2009 | |
| WO | 2009140636 | 11/2009 | |
| WO | 2010039853 | 4/2010 | |
| WO | 2010057286 | 5/2010 | |
| WO | 2010059839 | 5/2010 | |
| WO | WO-2010059839 A2 * | 5/2010 | ........... A61B 5/0803 |
| WO | 2010117810 | 10/2010 | |
| WO | WO2013023218 | 2/2013 | |

OTHER PUBLICATIONS

Goodall Article—Eleanor V. Goodhall et al., "Position-Selective Activation of Peripheral Nerve Fibers with a Cuff Electrode," IEEE Transaction on Biomedical Engineering, vol. 43, No. 8, Aug. 1996, pp. 851-856.

Naples Article—Gregory G. Naples et al., "A Spiral Nerve Cuff Electrode for Peripheral Nerve Stimulation," 8088 IEEE Transactions on Biomedical Engineering, 35. Nov. 1988, No. 11, New York, NY, pp. 905-915.

Oliven Article—Arie Oliven et al., "Upper airway response to electrical stimulation of the genioglossus in obstructive sleep apnea," Journal of Applied Physiology, vol. 95, pp. 2023-2029, Nov. 2003, www.jap.physiology.org on Sep. 18, 2006. (8 pages).

Schwartz Article—Alan R. Schwartz MD et al., Theraputic Electrical Stimulation of the Hypoglossal Nerve in Obstructive Sleep Apnea, Arch Otolaryngol Head And Neck Surg., vol. 127, Oct. 2001, pp. 1216-1223. Copyright 2001 American Medical Association. (8 pages).

Park, "Preoperative Percutaneous Cranial Nerve Mapping in Head and Neck Surgery," Arch Facial Plast Surg/vol. 5, Jan./Feb. 2003, www.archfacial.com pp. 86-91.

Stanescu, "Expiratory flow limitation during sleep in heavy snorers" European Respiratory Journal, 1996, 9, 2116-2121.

J Sleep Res., "Hypoglossal nerve stimulation improves obstructive sleep apnea: 12-month outcomes" Journal, 2014, 23, 77-83.

(56) References Cited

OTHER PUBLICATIONS

The Laryngoscope, "Implanted Upper Airway Stimulation Device for Obstructive Sleep Apnea" Journal, 2012, 122, 1626-1633.

* cited by examiner

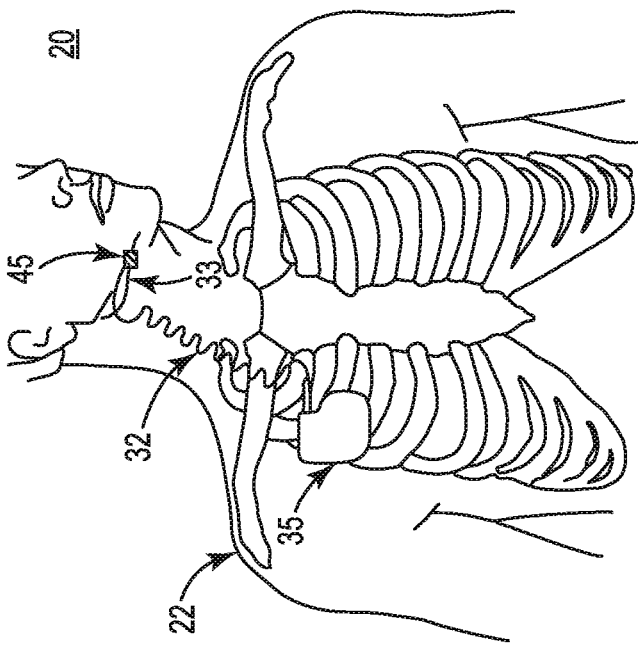
Fig. 2A
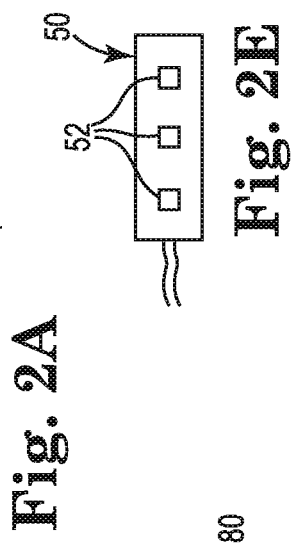
Fig. 2E
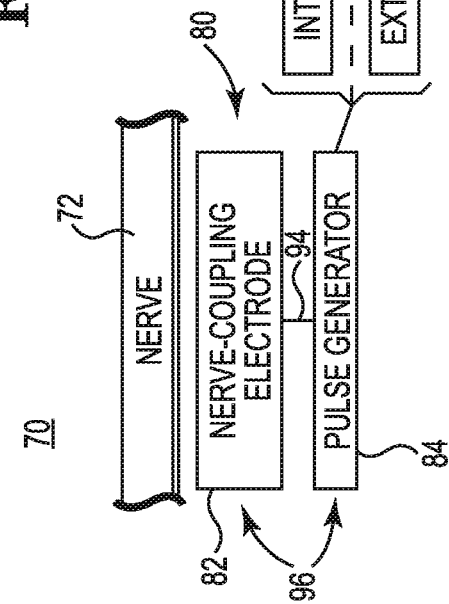
Fig. 2D
Fig. 1B
Fig. 1A
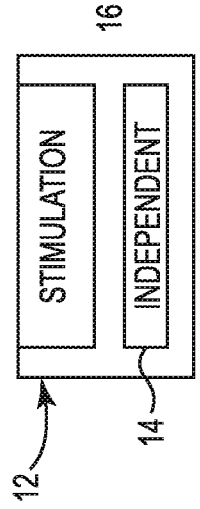
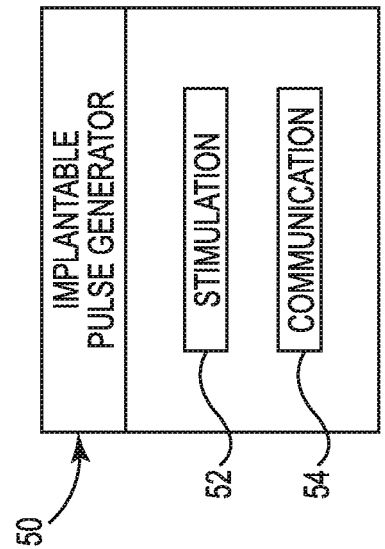
Fig. 2B
Fig. 2C

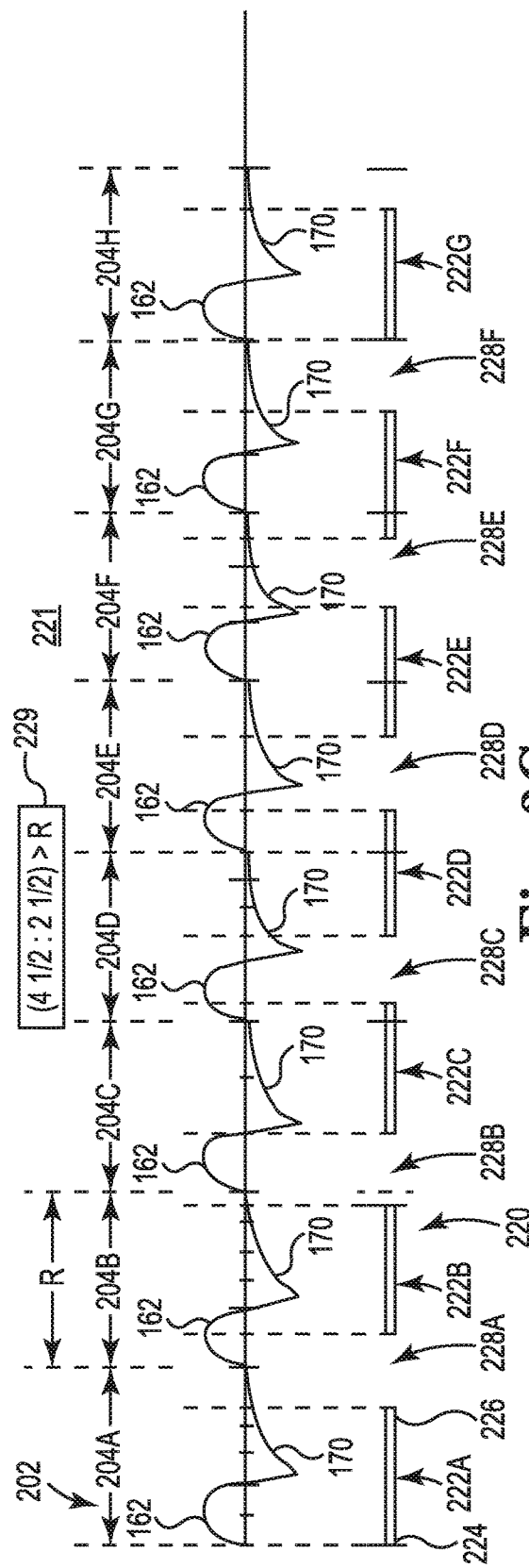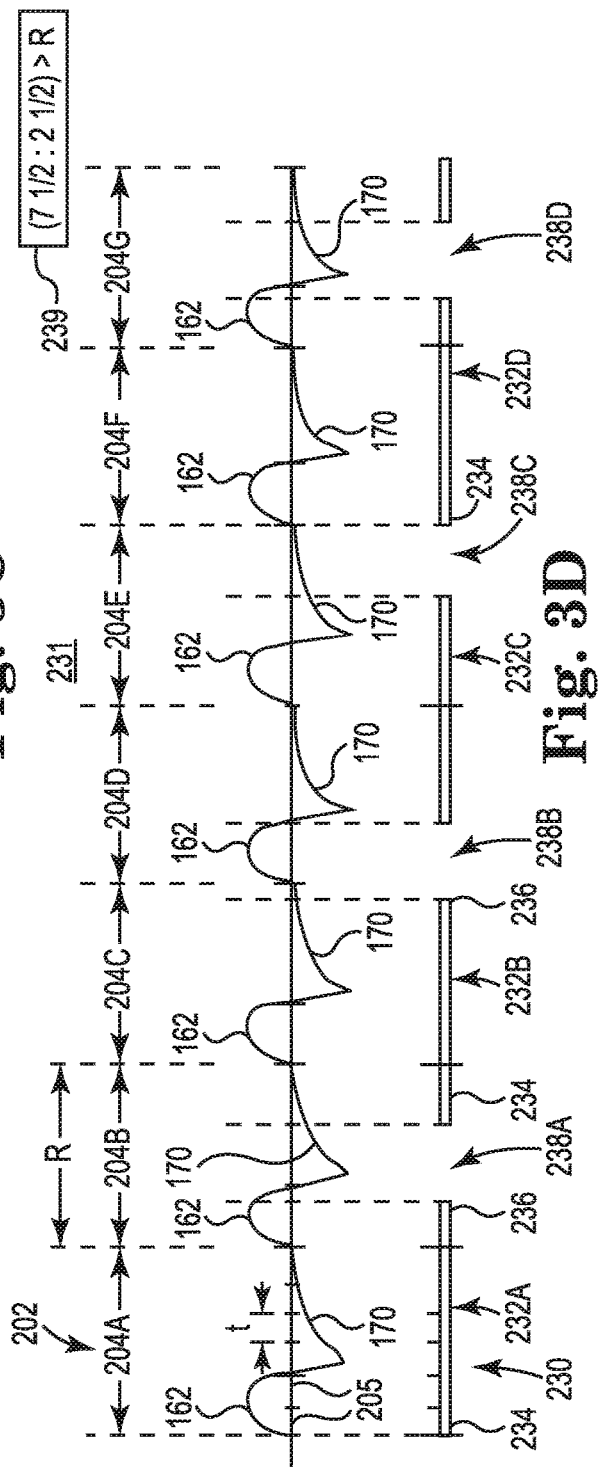

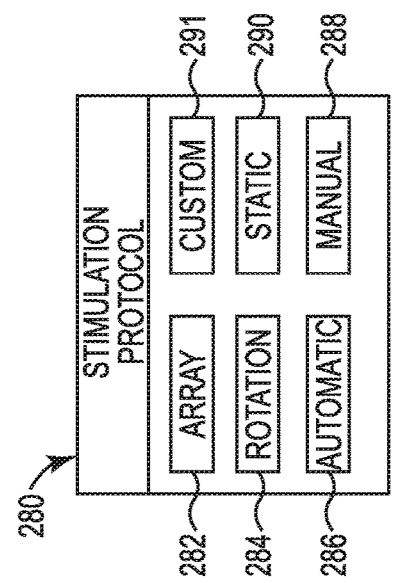
Fig. 5
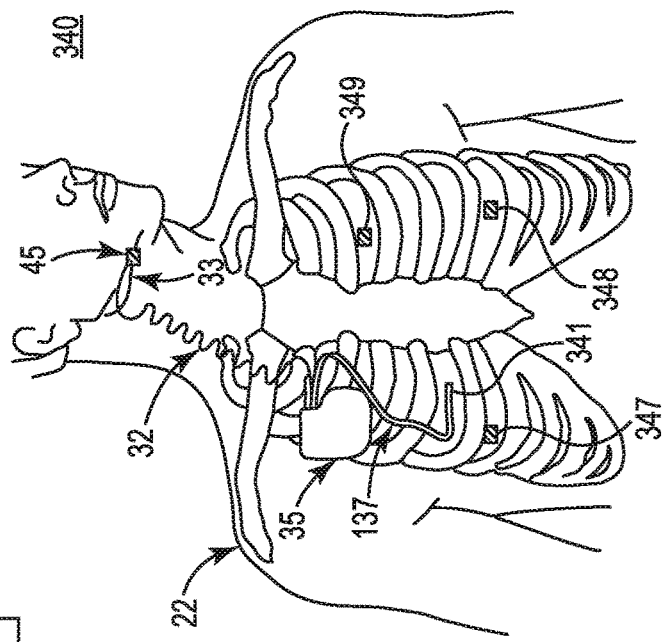
Fig. 7B
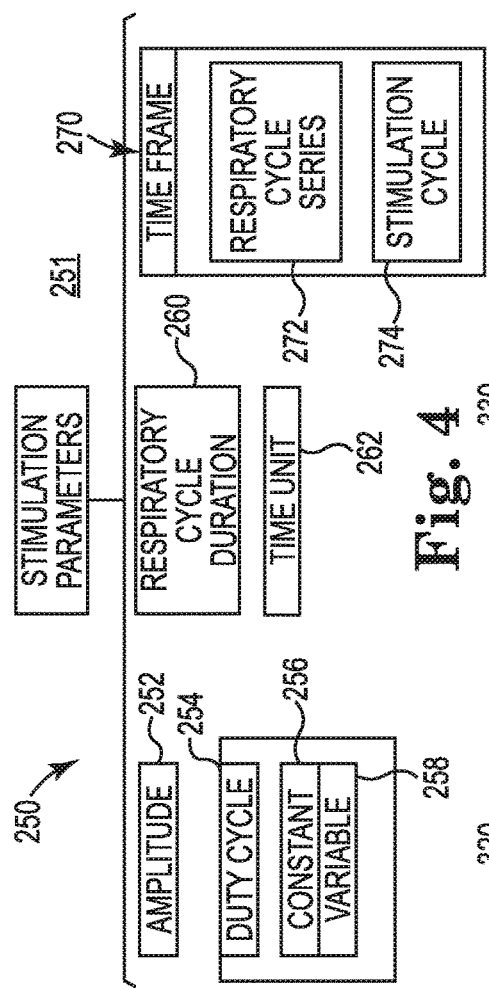
Fig. 4
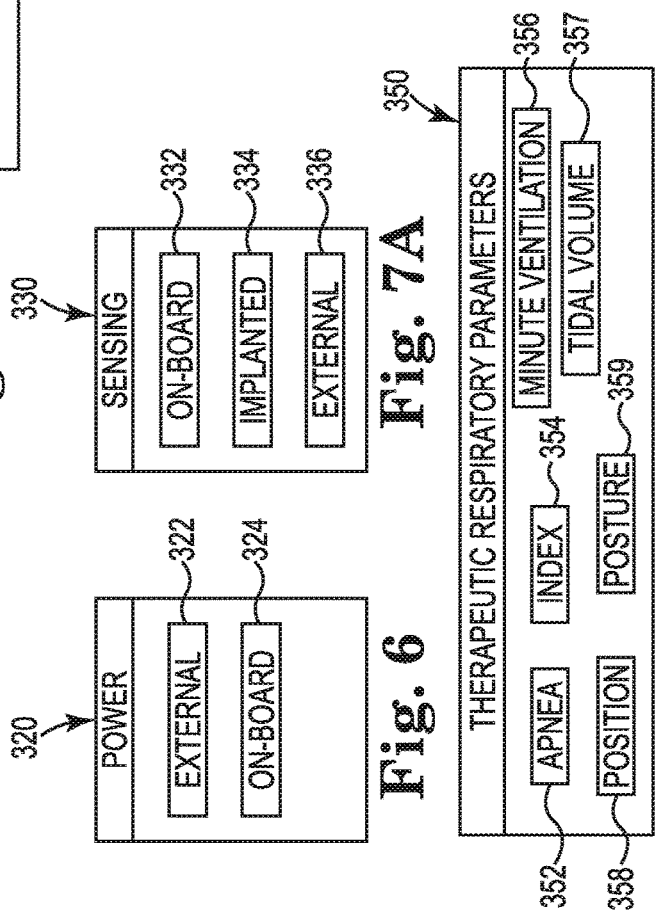
Fig. 7A
Fig. 6
Fig. 8

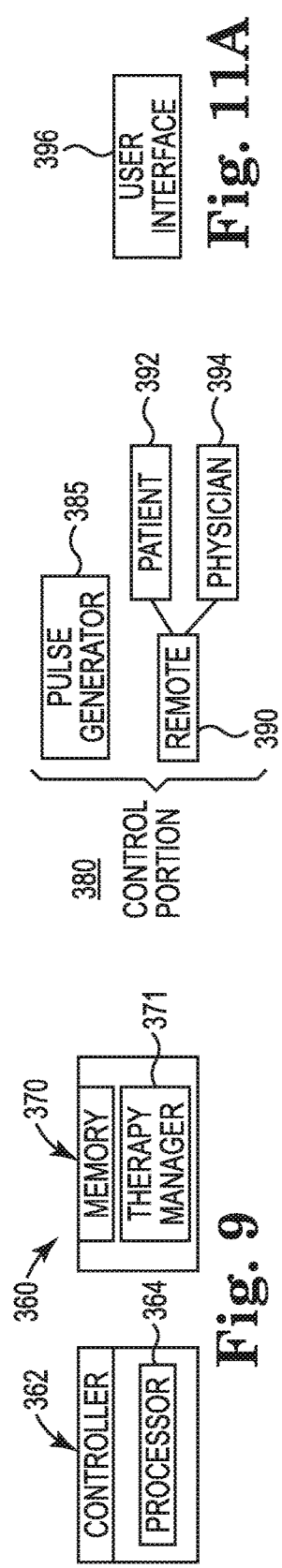
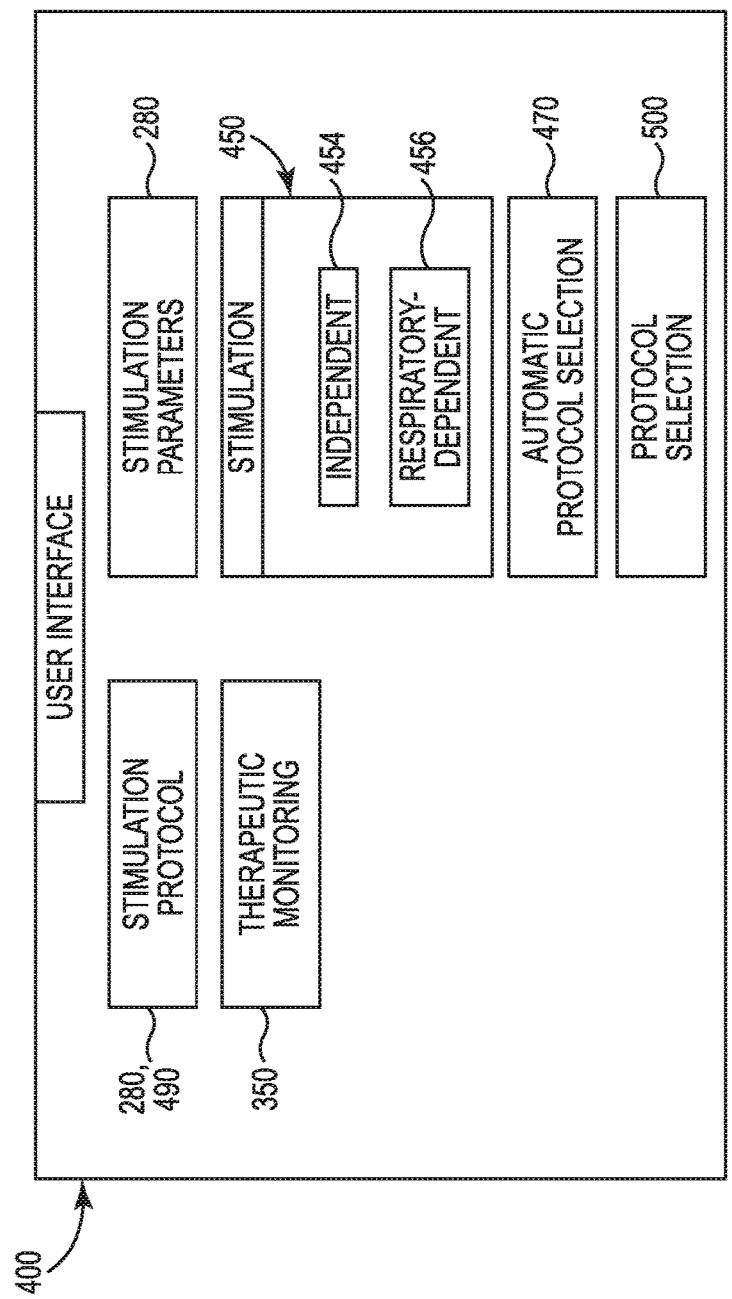

STIMULATION FOR TREATING SLEEP DISORDERED BREATHING

CROSS-REFERENCE TO RELATED APPLICATIONS

This 371 National Phase Application claims benefit of PCT Patent Application No. PCT/US2016/022611, filed Mar. 16, 2016, entitled STIMULATION FOR TREATING SLEEP DISORDERED BREATHING, which claims benefit from U.S. Provisional Patent Application 62/135,305, filed Mar. 19, 2015, both of which are incorporated by reference herein.

BACKGROUND

Targeted electrical stimulation of a nerve shows great promise in a number of therapies. In one example, such stimulation of a hypoglossal nerve is known to alleviate obstructive sleep apnea by helping to maintain and/or restore upper airway patency.

BRIEF DESCRIPTION OF THE DRAWINGS

FIG. 1A is a block diagram schematically illustrating a stimulation element, according to one example of the present disclosure.

FIG. 1B is a block diagram schematically illustrating a therapy manager, according to one example of the present disclosure.

FIG. 2A is a diagram schematically illustrating an at least partially implantable stimulation system relative to a patient, according to an example of the present disclosure.

FIG. 2B is a block diagram schematically illustrating an implantable pulse generator, according to one example of the present disclosure.

FIG. 2C is a block diagram schematically illustrating a control portion for the at least partially implantable stimulation system, according to one example of the present disclosure.

FIG. 2D is block diagram schematically illustrating a stimulation system, according to one example of the present disclosure.

FIG. 2E is top view schematically illustrating a stimulation electrode, according to one example of the present disclosure.

FIG. 3C is a diagram schematically illustrating a series of reference respiratory cycles juxtaposed relative to a stimulation protocol, according to one example of the present disclosure.

FIG. 3D is a diagram schematically illustrating a series of reference respiratory cycles juxtaposed relative to a stimulation protocol, according to one example of the present disclosure.

FIG. 4 is a block diagram schematically illustrating a plurality of stimulation parameters, according to one example of the present disclosure.

FIG. 5 is a block diagram schematically illustrating a stimulation protocol element, according to one example of the present disclosure.

FIG. 6 is a block diagram schematically illustrating power source components of the at least partially implantable stimulation system, according to one example of the present disclosure.

FIG. 7A is a block diagram schematically illustrating a sensing element of the at least partially implantable stimulation system, according to one example of the present disclosure.

FIG. 7B is a diagram schematically illustrating an at least partially implantable stimulation system relative to a patient and including sensing elements, according to an example of the present disclosure.

FIG. 8 is a block diagram schematically illustrating therapeutic respiratory parameters, according to one example of the present disclosure.

FIG. 9 is a block diagram schematically illustrating a control portion of an at least partially implantable stimulation system, according to one example of the present disclosure.

FIG. 10 is a block diagram schematically illustrating aspects of a control portion, according to one example of the present disclosure.

FIG. 11A is a block diagram schematically illustrating a user interface, according to one example of the present disclosure.

FIG. 11B is a block diagram schematically illustrating a user interface, according to one example of the present disclosure.

DETAILED DESCRIPTION

Figure 3A:
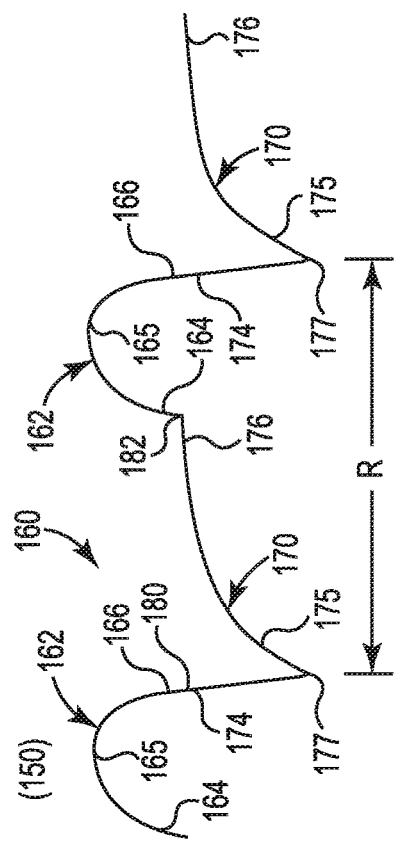
FIG. 3A is a diagram schematically illustrating a respiratory cycle in one example breathing pattern, according to one example of the present disclosure.

In the following Detailed Description, reference is made to the accompanying drawings, which form a part hereof, and in which is shown by way of illustration specific examples in which the invention may be practiced. In this regard, directional terminology, such as "top," "bottom," "front," "back," "leading," "trailing," etc., is used with reference to the orientation of the Figure(s) being described. Because components of examples can be positioned in a number of different orientations, the directional terminology is used for purposes of illustration and is in no way limiting. It is to be understood that other examples may be utilized and structural or logical changes may be made without departing from the scope of the present disclosure. The following detailed description, therefore, is not to be taken in a limiting sense.

At least some examples of the present disclosure are directed to methods of treating obstructive sleep apnea via applying nerve stimulation. By doing so, upper airway patency may be maintained and/or increased while preventing or minimizing collapse of the upper airway. At the same time, by using targeted stimulation, one can limit the overall volume of stimulation applied to a given nerve or set of nerves.

In some examples, nerve stimulation is applied during a treatment period. In some examples, a treatment period corresponds to the patient engaging in sleeping behavior, and during which sleep disordered breathing is to be avoided. The treatment period can be manually initiated by the patient or automatically initiated by a device that applies the nerve stimulation.

In some examples, an at least partially implantable stimulation system for treating sleep disordered breathing includes an independent stimulation element to stimulate an airway-patency-related nerve without synchronization relative to characteristics of respiratory wave form. Accordingly, in some examples, the independent stimulation element forms part of a system that omits any sensing elements. In some examples, the stimulation element comprises a stimulation engine to determine and administer a stimulation protocol. In some examples, the stimulation element further includes and/or acts in cooperation with a pulse generator and stimulation electrode to deliver the stimulation to a target nerve. In such examples, the pulse generator includes the stimulation engine or the stimulation engine is in communication with the pulse generator. In some examples, the pulse generator is implantable and in some examples, the pulse generator is external to the patient's body. In some examples, the stimulation element is in communication with a therapy manager or is incorporated within a therapy manager. In some examples, the therapy manager is in communication with the pulse generator and/or incorporated within the pulse generator. In some examples, at least some components, functions, elements, etc. of the therapy manager are incorporated within a physician programmer external to the patient or a patient remote external to the patient.

In some examples, the at least partially implantable stimulation system includes sensing element(s) to receive and/or obtain respiratory information but that information is not employed to trigger stimulation by synchronizing the stimulation relative to characteristics of the sensed respiratory waveform. Rather, in these examples, the sensed respiratory information is used to detect and evaluate sleep disordered breathing behavior. When the detected behavior meets or exceeds a severity threshold, the therapy manager generally activates stimulation via the independent stimulation element. In some examples, the severity threshold is based on at least a frequency and/or an intensity of apneic events. In some instances, the severity threshold also may be expressed as an obstructive sleep apnea (OSA) burden, i.e. a quantity and/or intensity of apneas which are occurring. In some examples, the severity threshold or OSA burden is expressed as an Apnea-Hypopnea Index (AHI). However, despite the respiratory sensing occurring in these examples, the stimulation is performed via a protocol that remains independent of the particular characteristics of a real-time sensed respiratory waveform. In other words, individual stimulation periods are not triggered and/or synchronized relative to respiratory characteristics, such as the inspiratory phase.

In some examples, the independent stimulation element is configured to asynchronously stimulate an airway-patency-related nerve, according to a first stimulation protocol independent of sensed respiratory information and in which each stimulation cycle includes a stimulation period and a non-stimulation period. In some instances, the first stimulation protocol is referred to as being independent because the first stimulation protocol is not synchronized relative to sensed respiratory information. In some instances, the independence of the first stimulation protocol also may be referred to as being an asynchronous stimulation protocol because the first stimulation protocol is not synchronized relative to the sensed respiratory information.

In some examples, each stimulation period within a stimulation cycle includes continuous stimulation. In some examples, continuous stimulation refers to a train of stimulation pulses which occur in a relatively short time frame. For instance, in some examples, continuous stimulation corresponds to at least a finite number (e.g. 5, 10, etc.) of stimulation pulses per second. In some examples, continuous stimulation corresponds to at least 20 stimulation pulses per second. In some examples, continuous stimulation corresponds to at least 30 stimulation pulses per second. In some examples, the number of stimulation pulses per second is selectable by an operator via a control portion (e.g. 56 in FIG. 2C).

In some examples, during the above-described continuous stimulation, each stimulation pulse within a train of stimulation pulses includes a primary stimulation pulse followed by a separate recharge pulse, which is in turn followed by a non-stimulation phase before the next primary stimulation pulse.

In some examples, the stimulation period has a minimum duration equal to or greater than an inspiratory reference. In some examples, the inspiratory reference corresponds to a duration of an inspiratory phase of a reference respiratory cycle. In some examples, each stimulation cycle of the first stimulation protocol includes the stimulation period having a duration greater than a duration of the inspiratory reference followed by the non-stimulation period, which has a duration less than the duration of the stimulation period.

In some examples, the reference respiratory cycle is defined by a historical patient-specific average respiratory cycle for stable respiration. In some examples, the reference respiratory cycle is defined by a multi-patient average respiratory cycle for stable respiration.

Because the overall duration of the stimulation cycle (both stimulation period and non-stimulation period) intentionally does not match the duration (R) of the reference respiratory cycle in at least some examples, the stimulation protocol ensures that each successive stimulation period within the series of stimulation cycles will fall along a different portion of each of the successive reference respiratory cycles. Accordingly, even though the stimulation is not synchronized relative to a characteristic (e.g. inspiration) of reference respiratory waveform (which includes the series of reference respiratory cycles), no matter where the stimulation protocol is started relative to the ongoing pattern of reference respiratory cycles, the stimulation period of each stimulation cycle will overlap with at least a portion of the inspiratory phase of the respective reference respiratory cycles for a significant majority of the treatment period. Accordingly, even if the stimulation protocol happens to be initiated at a time that the non-stimulation period of the initial stimulation cycle at least partially overlaps with the inspiratory phase of a reference respiratory cycle, the stimulation periods of the successive stimulation cycles will at least partially overlap the inspiratory phase of the next reference respiratory cycles. Moreover, at least some of the later successive stimulation periods will significantly overlap (e.g. overlap at least a majority of the inspiratory phase) the inspiratory phase of the at least some of the respective successive reference respiratory cycles. In some instances, such significant overlap may include a complete overlap of the inspiratory phase.

Via this arrangement, it becomes feasible to stimulate an airway-related-nerve to treat sleep disordered breathing either without any sensing elements at all or with minimal use of sensing elements. In this sense, the stimulation is performed asynchronously, i.e. without synchronization relative to sensed respiratory information. Among other benefits, this may reduce the cost of the stimulation system, may simplify its implantation, and may simplify operation of the stimulation system. Moreover, the presence of non-stimulation periods helps to minimize potential muscle fatigue that might otherwise be caused. Finally, providing asynchronous stimulation via the independent stimulation element may help to overcome situations in which sensor-based systems or synchronous systems are unable to achieve synchronization and/or the sensing signal become unstable (or is unavailable).

However, it will be understood that in some examples, an asynchronous independent stimulation protocol is implemented while still performing sensing respiratory information for non-synchronization purposes, such as evaluating stimulation therapy effectiveness and/or provide information to adjust parameters of the independent stimulation protocol.

In another aspect, providing stimulation asynchronously via the independent stimulation element may enable leveraging a greater number of different stimulation protocols because of fewer constraints on how the stimulation cycles of the stimulation protocols relate to characteristics of a respiratory waveform. Moreover, in some examples, the stimulation element applies nerve stimulation while rotating application through the plurality of different stimulation protocols, which in some instances provides a more robust therapy than using a single stimulation protocol. In some examples, this rotation also can be used to sort through the relative effectiveness of the different stimulation protocols and select the most effective stimulation protocol for a particular patient.

In some examples, an independent stimulation protocol is implemented in which the inspiratory phase of a majority of reference respiratory cycles are at least partially overlapped by a stimulation period, with more occurrences of such overlapping being preferred over fewer such occurrences. Similarly, in some examples, it is generally preferred to implement such an independent stimulation protocol via providing the sequence of stimulation periods to result in a greater degree of overlap with the inspiratory phase of the reference respiratory cycles rather than a lesser degree of overlap.

In some examples, the therapy manager includes a stimulation protocol element that provides convertible operation between the above-described independent (i.e. asynchronous) first stimulation mode and a synchronous second stimulation mode of stimulating the airway-patency-related nerve synchronous with a characteristic of the sensed respiratory waveform. In this arrangement, the therapy manager causes: operation in the first stimulation mode for at least a first predetermined period of time; conversion of operation into the second stimulation mode upon at least one parameter of the sensed respiratory waveform meeting a sensor signal quality criteria; and reversion of operation into the first stimulation mode for at least the first predetermined period of time upon the at least one parameter of the sensed respiratory waveform failing to meet the sensor signal quality criteria. Accordingly, in one aspect, the first stimulation mode comprises the default mode of stimulation.

In some examples, the conversion between the first stimulation mode and the second stimulation mode is automatic. In some examples, the therapy manager includes a user selection function to enable user selection of either the first mode or the second mode as a default mode.

In some examples, the therapy manager includes an operator selection function to selectively cause conversion between the two different stimulation modes. In one aspect, such selective conversion can be implemented manually during operator titration of the therapeutic treatment as the operator adjusts parameters of the stimulation protocols for a particular patient.

In some examples the first predetermined period of time corresponds to a period sufficient to establish a steady state in which filtering is established, inspiration and expiration are being detected reliably, signal gain control is realized, etc. In some examples, the first predetermined period of time does not correspond to a test mode for evaluating the operational fitness of the stimulation system. Stated differently, activities occurring during the first predetermined period of time may sometimes be referred to as a non-test mode.

Via this arrangement, the independent stimulation element first establishes a stable respiratory pattern. This arrangement therapeutically achieves airway patency while simultaneously increasing the likelihood of later successful synchronization of a respiratory-dependent stimulation protocol. In particular, because some examples dictate that stimulation is not implemented until or unless sleep disordered breathing behavior (above a severity threshold) is detected, the available respiratory signal will likely be a poor signal which attempt synchronization of a stimulation signal.

Accordingly, rather than attempt a likely problematic synchronization, at least some examples of the present disclosure first establish independent nerve stimulation that does not depend on synchronization. This independent stimulation, in turn, helps to establish a stable respiratory pattern or signal, which then in turn, significantly increases the success of later synchronizing a respiratory-dependent stimulation protocol relative to the respiratory signal. Once a robust synchronization is established, then the system is well positioned to maintain a stable respiratory period using less overall stimulation by stimulating on a synchronized basis in which stimulation is limited to generally coinciding with an inspiratory phase (or other characteristic of the sensed respiratory waveform).

Of course, in the event the sensed respiratory signal changes in a way that hinders synchronization and/or delivery of effective therapeutic stimulation, then in at least some examples, the therapy manager will cause operation to revert to the independent stimulation mode.

With this arrangement, the independent stimulation mode enables initially applying a higher intensity stimulation to establish and ensure a stable respiratory pattern, which in turn, increases the likelihood of being able to later establish and maintain a lower intensity stimulation via the synchronized, respiratory-dependent stimulation mode. In this way, it is expected that overall muscle fatigue is minimized because of the likelihood of the synchronization mode successfully operating for a longer period of time than if the independent stimulation mode were not applied first.

Accordingly, in some examples, an independent stimulation element is implemented alone to treat sleep disordered breathing. However, in some examples, treatment is accomplished via a complementary combination of an independent (i.e. asynchronous) stimulation mode and a synchronous stimulation mode.

As noted above, in some examples, a stimulation protocol element may provide convertible operation between the above-described independent (i.e. asynchronous) first stimulation mode and a synchronous second stimulation mode of stimulating the airway-patency-related nerve synchronous with a characteristic of the sensed respiratory waveform. However, in one example arrangement, the therapy manager causes: operation in the second stimulation mode and conversion of operation into the first stimulation mode upon at least one parameter of the sensed respiratory waveform failing to meet a sensor signal quality criteria. Later, reversion of operation into the second stimulation mode is made upon the at least one parameter of the sensed respiratory waveform meeting the sensor signal quality criteria. Accordingly, in one aspect, the second stimulation mode comprises the default mode of stimulation.

These examples, and other examples, are further described in association with at least FIGS. 1-19.

FIG. 1A is block diagram schematically illustrating a stimulation element 12, according to one example of the present disclosure. In some examples stimulation element 12 directs and controls nerve stimulation to treat obstructive sleep apnea. In some examples, stimulation element 12 includes an independent stimulation function 14, which in general terms, applies electrical stimulation via a stimulation protocol to an airway-patency-related nerve to treat upper airway obstructions. In some examples, such airway-patency-related nerves include at least the protrusor branches of the hypoglossal nerve.

In some examples, the independent stimulation function 14 operates to stimulate an airway-patency-related nerve, according to a first stimulation protocol not synchronized relative to sensed respiratory information and in which each stimulation cycle includes a stimulation period and a non-stimulation period. Accordingly, in some examples, via the independent stimulation function 14, nerve stimulation is applied independent of characteristics of sensed respiratory information. In other words, once the independent stimulation function 14 has been activated, the initiation and termination of individual nerve stimulation periods is not synchronized relative to a characteristic, such as onset of the inspiratory phase of the patient respiratory cycle and/or other characteristics. In at least this context, operation of independent stimulation function 14 (FIG. 1A) may be referred to as an asynchronous stimulation function or mode.

In some examples, once a treatment period begins, such as when the patient is engaging in sleeping behavior (and during which sleep disordered breathing is to be avoided), the nerve stimulation function 14 is always in an "on" or active mode, and therefore stimulation cycles are applied to the nerve. In such examples, activation or deactivation of the independent stimulation function 14 is independent of whether or not apneas are occurring. For instance, the general activation and/or deactivation of the independent stimulation function 14 can be controlled according to a selectable time schedule, such as a predetermined start time (e.g. 10 p.m.) and predetermined end time (e.g. 6 a.m.).

FIG. 1B is a block diagram schematically illustrating a therapy manager 16, according to one example of the present disclosure. In general terms, therapy manager 16 directs a therapeutic regimen for controlling sleep disordered breathing such as, but not limited to, obstructive sleep apnea. The therapy manager 16 operates as part of, or in cooperation with, an at least partially implantable nerve stimulation system. In some examples, therapy manager 16 forms at least part of a control portion such as, but not limited to, control portion 360 as later described in association with at least FIGS. 9-10, and as such, in some examples, therapy manager 16 includes at least some of substantially the same features and attributes as therapy manager 371 described in association with at least FIG. 9.

In some examples, therapy manager 16 is in communication with and/or incorporates at least some aspects of stimulation element 12. In some examples, the therapy manager has access to physiologic sensing information via sensing elements (e.g. at least FIGS. 7A-7B). In such examples, general activation and/or general deactivation of the independent stimulation function 14 is controlled according to a likelihood of sleep behavior, which is determined according to at least body position, body posture, body motion, and/or body activity parameters, which can be sensed via an accelerometer or other sensing elements. In some examples, determining likelihood of sleep behavior is supplemented via additional sensed physiologic information, including but not limited to sensed respiratory information.

In some of the examples in which the therapy manager 16 has access to sensed physiologic information (at least FIGS. 7A-8), once a treatment period begins, the nerve stimulation function 14 is not generally activated and/or deactivated to stimulate a nerve until prompted to do so based on respiratory behavior criteria (e.g. whether apneas are likely or are occurring, etc.). This determination is separate from, and independent of, timing or synchronizing individual stimulation periods relative to particular characteristics (e.g., inspiration, expiration, etc.) of sensed respiratory information. Accordingly, in these examples, whether or not a patient receives any stimulation at all is governed by whether or not the patient experiences a sufficient quantity, frequency, or intensity of apneas.

In other words, in some examples, therapy manager 16 operates to apply stimulation when the patient is experiencing apneas or likely to experience apneas. In this way, nerve stimulation is limited to an as needed basis, thereby conserving energy of the stimulation system 20 and reducing potential muscle fatigue. As to the particular strength of the stimulation signal and whether it is applied in view of the relative severity of the sleep disordered respiratory behavior, at least some examples of automatic adjustment of a level of stimulation therapy is described in at least Christopherson, METHOD OF TREATING SLEEP DISORDERED BREATHING, published on Oct. 27, 2011 as US 2011-0264164.

In some examples, the detection of flow limitations and/or associated apneas, as well as the detection of the beginning and end of the respective inspiratory and expiratory phases of the respiratory cycle, is performed according to, or in cooperation with, known methods and devices for doing so. Some non-limiting examples of such devices and methods to recognize and detect the various features and patterns associated with respiratory effort and flow limitations include, but are not limited to: PCT Publication WO/2010/059839, titled A METHOD OF TREATING SLEEP APNEA, published on May 27, 2010; Christopherson U.S. Pat. No. 5,944,680, titled RESPIRATORY EFFORT DETECTION METHOD AND APPARATUS; and Testerman U.S. Pat. No. 5,522,862, titled METHOD AND APPARATUS FOR TREATING OBSTRUCTIVE SLEEP APNEA.

In some examples, the stimulation element 12 comprises a stimulation engine to determine and administer a stimulation protocol. In some examples, the stimulation element 12 further includes and/or acts in cooperation with a pulse generator and stimulation electrode to deliver the stimulation to a target nerve, such as later described in association with at least FIGS. 2A-2D and 7B. In such examples, the pulse generator includes the stimulation engine or the stimulation engine is in communication with the pulse generator.

In some examples, the therapy manager 16 is in communication with the pulse generator and/or incorporated within the pulse generator. In some examples, at least some components, functions, elements, etc. of the therapy manager 16 are incorporated within a physician programmer external to the patient or a patient remote external to the patient.

Details regarding particular stimulation protocols implemented via the independent stimulation function 14 are later described in association with at least FIGS. 3B-3E. In particular, at least some details are provided regarding how asynchronous stimulation may increase therapeutic effectiveness in treating sleep disordered breathing.

FIG. 2A is a schematic diagram of an at least partially implantable stimulation system 20, according to an example of the present disclosure. In general terms, the stimulation element 12 of FIG. 1A (and/or therapy manager 16 of FIG. 1B) is incorporated within and/or operates in association with stimulation system 20 to deliver stimulation.

As illustrated in FIG. 2A, in one example system 20 includes an implantable pulse generator (IPG) 35 and a stimulation lead 32 electrically coupled with the IPG 35 via a connector (not shown) positioned within a connection port of the IPG 35. In some examples, the IPG 35 is surgically positioned within a pectoral region of a patient 22. The lead 32 includes a stimulation electrode portion 45 and extends from the IPG 35 so that the stimulation electrode portion 45 is positioned in contact with a desired nerve, such as an airway-patency-related nerve 33 of the patient 10, to enable stimulation of the nerve 33, as described below in detail. In some examples, the stimulation electrode portion 45 comprises a self-sizing cuff such as described in U.S. Pat. No. 8,340,785 to Bonde et al. In some examples, in association with electrode 45, lead 32 includes at least some of the features and attributes described in U.S. Patent Publication 20110160827 to Bonde et al. In some examples, lead 32 includes features and attributes at least consistent for use in an implantable stimulation system as described in U.S. Pat. No. 6,572,543 to Christopherson et al.

As later described more fully in association with at least FIGS. 9-10, in some examples the therapy manager 16 controls the IPG 35, and is implemented externally of the IPG 35, entirely within the IPG 35, or partially within the IPG 35.

In some examples, stimulation electrode portion 45 comprises a cuff electrode including a single operative contact group of at least two electrodes through which the stimulation is deliverable non-selectively to the airway-patency-related nerve. FIG. 2E is a top view schematically illustrating one example of such an electrode 50 including a single operative contact group of at least two electrodes 52. In some examples, the stimulation electrode portion 45 comprises a cuff electrode including at least one operative contact group through which the stimulation is deliverable non-selectively to the airway-patency-related nerve. Accordingly, more than one operative contact group of electrodes can be incorporated in a single cuff electrode. In some examples, the stimulation electrode portion 45 can include multiple, separate cuff electrodes with each having at least one operative contact group of electrodes.

In some examples, the stimulation system for treating obstructive sleep apnea is a totally implantable system which provides therapeutic solutions for patients diagnosed with obstructive sleep apnea. However, in some examples, one or more components of the system are not implanted in a body of the patient, thereby providing an at least partially implantable system. A few non-limiting examples of such non-implanted components include an external processing unit and/or an external power source, as later noted in association with at least FIG. 6.

In some examples, the at least partially implantable stimulation system 20 does not include any sensing elements. Accordingly, to the extent that the system 20 and its therapy manager 16 apply stimulation protocols to treat respiratory behavior, any patient-specific respiratory information would be received and/or obtained prior to, and/or during, implantation of the system 20. Alternatively, a temporary external sensing system could be employed to periodically calibrate and/or evaluate therapeutic efficacy of the at least partially implantable stimulation system 20 operating according to an independent stimulation function 14 (FIG. 1A).

At least some examples of the sensor-less stimulation system 20 use significantly less power than some sensor-based systems and are easier to implant. Moreover, in such examples, the system 20 is significantly easier to construct and/or operate because the sensors, certain sensing-related circuitry, and certain operational programming can be omitted.

However, it will be understood that in some examples, the stimulation system 20 includes sensing elements, at least in the manner later described in association with at least FIGS. 7A-7B. In at least some of these examples, the sensing elements are used to evaluate therapy and particular stimulation protocols but are not used to synchronize stimulation relative to characteristics of the sensed respiratory waveforms.

FIG. 2B is block diagram of an implantable pulse generator (IPG) 50, according to one example of the present disclosure. In some examples, IPG 50 includes at least some of substantially the same features and attributes as IPG 35 (FIG. 2A). However, in some examples, IPG 50 includes at least some features and attributes different than those in IPG 35 (FIG. 2A). As such, in some examples, IPG 50 can take different forms and be implanted in locations other than those shown in FIG. 2A (and also FIG. 7B).

With further reference to FIG. 2B, in some examples the implantable pulse generator 50 includes a stimulation element 52 and a communication element 54. The stimulation element 52 generates and applies a neuro-stimulation signal via electrode(s) (such as stimulation electrode(s) 45 in FIG. 2A) according to a treatment regimen programmed by a physician and/or in cooperation with therapy manager 16. In some examples, stimulation element 52 comprises at least some of substantially the same features and attributes as stimulation element 12 as previously described in association with FIG. 1A.

The communication element 54 provides a communication pathway to enable transmission of data, power, and/or controls signals both to and from the implanted portions of the system 20 relative to the external portions of the system 20. For instance, in some examples, the communication element 54 is configured to report activities of the IPG 50 (including sensed physiologic data, stimulation history, number of apneas detected, etc.) and is configured to receive initial or further programming of the IPG 50 from an external source, such as a patient programmer, clinician programmer, etc. as later noted in association with at least FIG. 10. In some examples, the communication element 54 utilizes a radiofrequency (RF) telemetry link or other wireless communication protocols.

In some examples, the implantable pulse generator 50 includes a control portion or at least part of a control portion such as control portion 56 shown in FIG. 2C. In general terms, control portion 56 directs operation of the pulse generator 50 and the at least partially implantable stimulation system. Further details regarding such a control portion 56 are described later in association with at least FIGS. 9-10. Moreover, in some examples, control portion 56 is operable in association with a user interface, such as described later in association with at least FIGS. 11A-11B.

FIG. 2D is a block diagram 70 schematically illustrating an at least partially implantable stimulation system 80, according to an example of the present disclosure. In some examples, system 80 includes at least some of substantially the same features and attributes as system 20 (FIG. 2A), pulse generator 50 (FIG. 2B), and control portion 56 (FIG. 2C), except for system 80 having some portions in a non-pectoral location and located in close proximity to a target nerve to be stimulated, as further illustrated in association with at least FIG. 2D.

In some examples, system 80 is a sensor-less system in a manner substantially similar to the above-described system 20. In other words, as at least partially implanted in the patient's body, system 80 omits a sensor.

As shown in FIG. 2D, in some examples system 80 includes a nerve-coupling electrode portion 82 and a pulse generator 84. In some examples, the nerve-coupling electrode portion 82 comprises an element which is at least electrically coupled relative to a target nerve 72 suitable to maintain or restore airway patency, such as but not limited to, the hypoglossal nerve.

In some examples, the electrode portion 82 comprises a cuff, such as one of the stimulation electrode portions 45 described in association with FIG. 2A in which the electrode portion is both mechanically and electrically coupled relative to the nerve 72. However, in some examples, the nerve-coupling electrode portion 82 comprises a cuff-less structure that is both mechanically and electrically coupled relative to the nerve 72.

In some examples, the nerve-coupling electrode portion 82 is not mechanically coupled to the nerve 72, but is mechanically coupled or secured in a location in close proximity to the nerve 72 and that enables electrically coupling of the electrode portion 82 relative to the nerve 72. In one instance, such examples include the electrode portion 82 being delivered to the target nerve 72 via a percutaneous access delivery. In one instance, such examples include the electrode portion 82 being delivered to the target nerve 72 via a transvenous delivery method in which the electrode portion 82 is delivered on a lead maneuvered within and through the vasculature of the patient.

In some examples, in a manner consistent with the previously described pulse generator 50 (FIG. 2B) pulse generator 84 includes a stimulation element 52 and a communication element 54. In some examples, pulse generator 84 includes solely internal components 90, which are internally within the body below the skin/tissue. However, in some examples, pulse generator 84 includes a combination of some internal components 90 and some external components 92, which are external to the body being above or outside the skin/tissue.

In some examples, via communication element 54 (FIG. 2B), system 80 includes a wired communication path 94 and/or a wireless communication path 96 between the pulse generator 84 and the nerve-coupling electrode portion 82, as shown in FIG. 2D. In some examples, either or both such communication pathways 94, 96 are also employable for communication between internal and external components 90, 92 of a pulse generator 84.

In some examples, in order to utilize and/or evaluate sensed respiratory information, the therapy manager 16 uses a reference point, such as a normal breathing pattern 150, as shown in FIG. 3A. Of course, variances may exist from patient-to-patient so it will be understood that the normal breathing pattern 150 is a representative example provided for illustrative purposes and is not intended to strictly define a breathing pattern that is universally normal for all patients. With this in mind, in some examples, the system 20 uses the particular breathing pattern of a specific patient (to which the method is applied) as the reference point to utilize and/or evaluate sensed respiratory information.

In the example of normal breathing pattern 150 shown in FIG. 3A, a respiratory cycle 160 includes an inspiratory phase 162 and an expiratory phase 170. The inspiratory phase 162 includes an initial portion 164, intermediate portion 165, and end portion 166 while expiratory phase 170 includes an initial portion 174, intermediate portion 175, end portion 176, and an expiratory peak 177. A first transition 180 occurs at a junction between the end inspiratory portion 166 and the initial expiratory portion 174 while a second transition 182 occurs at a junction between the end expiratory portion 176 and the initial inspiratory portion 164. In some instances, end expiratory portion 176 includes and/or is referred to as an expiratory pause that occurs just prior to onset of the initial inspiratory portion 164.

Figure 3B:
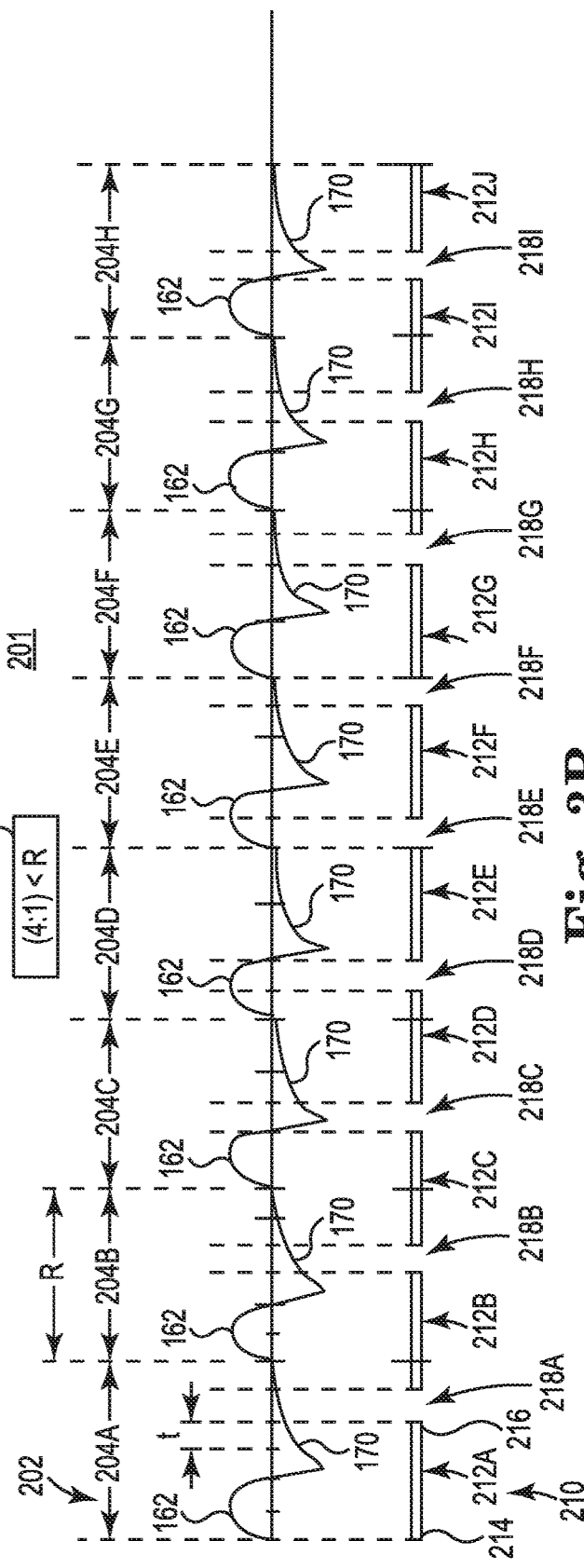
FIG. 3B is a diagram schematically illustrating a series of reference respiratory cycles juxtaposed relative to a stimulation protocol, according to one example of the present disclosure.

FIG. 3B is a diagram 200 schematically illustrating a stimulation protocol 210 implemented via independent stimulation function 14 (FIG. 1A), according to one example of the present disclosure. In some examples, after initializing the system according to the known/applicable respiratory cycle for that patient and after general activation of the independent stimulation function 14, the initiation, operation, and termination of the stimulation protocol 210 operates without regard to sensed respiratory information. In one aspect, FIG. 3B illustrates a respiratory pattern 202 including a series of reference respiratory cycles 204A-204H, with each cycle having substantially the same features and attributes as the respiratory cycle 160. Accordingly, each reference respiratory cycle 204A-204H has a duration R.

In one aspect, the pattern 202 represents a stable respiratory pattern that occurs during normal daytime breathing and/or that results from application of stimulation protocol 210.

In some examples, because stimulation via the stimulation protocol 210 is not synchronized relative to characteristics of actively-sensed respiratory cycles (such as via real-time measure of respiratory effort), the stimulation protocol 210 operates based on a reference respiratory cycle. In some examples, the reference respiratory cycle includes at least one of a historical patient-specific average respiratory cycle for stable respiration and a multi-patient average respiratory cycle for stable respiration. This historical and/or predictive information is employed in at least some examples in which the therapy manager 16 (FIG. 1B) is not actively sensing respiratory waveforms during operation of the at least partially implantable stimulation system 20.

As shown in FIG. 3B, stimulation protocol 210 includes a series of separate stimulation periods (e.g. pulses) 212A-212J spaced apart by a non-stimulation periods 218A-281I, each of which are interposed between an adjacent pair of stimulation periods. For instance, non-stimulation period 218B is interposed between stimulation periods 212B, 212C. In one aspect, each stimulation period (212A-212I) has a first end 214 and an opposite second end 216.

In some examples, in order to demonstrate the manner in which the stimulation protocol 210 is juxtaposed relative to the respiratory pattern 202, FIG. 3B further illustrates each respiratory cycle being apportioned into a discrete number (e.g. 3, 4, 5, 6, 7, 8, etc.) time units, with each time unit having a duration t. In the example shown in FIG. 3B, each respiratory cycle has a duration R and is divided into six time units t.

In some examples, the duration R is patient specific and is based on a long term average duration of a respiratory cycle. In some examples, the duration R is not patient specific and is based on an average duration of a respiratory cycle for many different patients. In some examples, duration R is about 3 to about 6 seconds. In some examples, via therapy manager 16, the duration R can be adjusted to a preferred duration. In some examples, the therapy manager 16 uses the patient-specific information regarding durations.

However, in some examples, where such information is not available or is problematic, the therapy manager 16 uses multi-patient information. For instance, for at least some patient populations a duration of an entire respiratory period is about 3 to 6 seconds, which corresponds to a general respiratory rate of about 10-18 breaths/minute. Moreover, generally speaking inspiration (e.g. an inspiratory phase) is a minority of the entire respiratory period which includes inspiration, expiration, and expiratory pause.

In at least some patient populations, an apnea and/or hypopnea has a minimum duration of about 10 seconds, which corresponds to a minimum duration about 2-3 breaths.

In some examples, an apnea may be avoided via implementation of a stimulation protocol which avoids missing (either completely missing or significantly missing) stimulation for more than one breath (e.g. one inspiratory phase).

With further reference to FIG. 3B, as represented by the legend 209, the stimulation protocol 210 operates according to a stimulation cycle in which the duration of the stimulation cycle is less than the duration (R) of the reference respiratory cycle. In some examples, the duration of the stimulation period exceeds the duration of the non-stimulation period by a factor of 3. In some examples, as shown by legend 209, the stimulation period and the non-stimulation period are in a proportion of 4 to 1. In such examples, each stimulation cycle includes a continuous stimulation period of 4 time units followed by a non-stimulation period of 1 time units, with this stimulation cycle being repeated continuously when nerve stimulation is generally activated. The total duration of the stimulation cycle (e.g. 4 time units of stimulation and 1 time unit of non-stimulation) is 5 time units, which is less than the duration R of the respiratory period, which is 6 time units in this example. In one aspect, this example arrangement in which the stimulation period is in much greater proportion to the non-stimulation period may benefit some patients by minimizing tongue rubbing by minimizing the frequency or total volume of tongue motion incident to tongue protrusion intentionally caused by the stimulation therapy to restore airway patency.

In FIG. 3B, the first end 214 of stimulation period 212A is shown as coinciding with the beginning of an inspiratory phase 162 of the respiratory cycle 204A. However, it will be understood that the beginning 214 of the stimulation period 212A is not synchronized relative to the inspiratory phase 162. Rather, the beginning 214 of stimulation period 212A is shown as coinciding with the beginning of inspiratory phase 162 for illustrative simplicity in juxtaposing the stimulation protocol 210 relative to the respiratory cycles 204A-204H. Accordingly, it will be understood that when stimulation (according to stimulation protocol 210) is initiated during a treatment period, the beginning of the stimulation period 212A may coincide with a different portion of the respiratory cycle (e.g. 204A) than shown in FIG. 3B.

With further reference to the stimulation protocol 210 in FIG. 3B, in one aspect, each respective non-stimulation period 218A-218I has a duration less than a duration of each respective stimulation periods 212A-212J. In one aspect, the duration of the stimulation period 212A is less than a duration (R) of the reference respiratory cycle 204A. In one aspect, the relative duration of the respective stimulation periods (e.g. 212A) and non-stimulation periods (e.g. 218A) causes each successive stimulation period (e.g. 212B) to begin at a different place along a successive respiratory cycle, such that the stimulation pattern is independent of (i.e. not synchronized relative to) the characteristics of the respiratory cycle. For instance, it can be seen from FIG. 3B that the first end 214 of stimulation period 212D coincides with a portion of the expiratory phase 170 of respiratory cycle 204C while the first end 214 of stimulation period 212E coincides with a portion of inspiratory phase 162 of the successive respiratory cycle 204D.

As shown in FIG. 3B, each of the respective stimulation periods 212A, 212B, 212C overlaps the entire inspiratory phase 162 of the respective respiratory cycles 204A-204C while stimulation period 212D at least partially overlaps the inspiratory phase 162 of respiratory cycle 204D.

Because the overall duration of the stimulation cycle (both stimulation period and non-stimulation period) does not match the duration (R) of the reference respiratory cycle, the stimulation protocol 210 ensures that each successive stimulation period within the series of stimulation cycles will fall along a different portion of the successive respiratory cycles. Accordingly, even though the stimulation is not synchronized relative to a characteristic (e.g. inspiration) of the respiratory waveform, no matter where the stimulation protocol 210 is started relative to a series of respiratory cycles, the stimulation periods will overlap with at least a portion of the inspiratory phase of the respective reference respiratory cycles for a significant majority of the treatment period. Accordingly, even if the stimulation protocol 210 happens to be initiated at a time that the non-stimulation period (e.g. 218D, 218E) at least partially overlaps with the inspiratory phase 162 of a respiratory cycle (e.g. 204D, 204E), the succeeding stimulation periods 212F, 212G, etc. at least partially overlaps the inspiratory phase 162 of the next respiratory cycle 204F, 204G, etc., with these later successive stimulation periods significantly overlapping (e.g. stimulation period 212F, which overlaps by at least a majority) or even completely overlapping (e.g. stimulation period 212G) the inspiratory phase 162 of the respective successive respiratory cycles (e.g. 204F, 204G).

In one aspect, in stimulation protocol 210 the duration of each stimulation period (e.g. 212A-212J) is less than a duration (R) of the reference respiratory cycles (204A-204H) but greater than a duration of the inspiratory phase 162 of an individual respiratory cycle (e.g. 204A).

In one aspect, a duty cycle for the stimulation cycle varies on a respiratory cycle-by-respiratory cycle basis. For instance, during respiratory cycles 204A, 204B, 204C, 204D, 204F, 204G, 204H the duty cycle is 5 time units of continuous stimulation and 1 time unit of non-stimulation, which equals about 83%. However, during respiratory cycle 204E, the duty cycle is 4 time units of continuous stimulation and 2 time units of non-stimulation, which equals about 67%. Every 5 respiratory cycles, the series of stimulation cycles repeats itself, as illustrated at respiratory cycle 204F, at which the first end 214 of the stimulation period 212G once again coincides with the beginning of the inspiratory phase 162 of the respiratory cycle 204F in a manner similar to respiratory cycle 204A. Accordingly, in one aspect, the long term duty cycle over an indefinite number of respiratory cycles (or average duty cycle over a sufficient number of time frames) is about 80%.

In some examples, via stimulation protocol 210, no sequence of four respiratory cycles occurs without a stimulation period significantly overlapping the inspiratory phase 162 (e.g. overlapping at least majority of the inspiratory phase 162) of respiratory cycles in FIG. 3B. This criteria is based on the longest period of time, in at least some examples, that a patient can go without a breath while avoiding a respiratory-event related arousal and/or to maintain near normal blood oxygenation.

In some examples, via stimulation element 12 (FIG. 1A) and/or therapy manager 16 (FIG. 1B) a clinician can implement a stimulation protocol in which a quantity (e.g. 2, 3, 4) is selected by the operator regarding how many respiratory cycles can pass without a significantly overlapping stimulation period, according to a predetermined amount of time and/or a predetermined number of respiratory cycles for a particular patient.

It will be understood that each inspiratory phase 162 of each respiratory cycle (204A-204H) is shown in its ideal form in FIG. 3B, and that in some instances where the inspiratory phase 162 at least partially coincides with one of the respective non-stimulation periods (e.g. 218D), the inspiratory phase may sometimes have an irregular shape compared to the idealized shape shown in FIG. 3B.

Accordingly, via stimulation protocol 210, the independent stimulation function 14 of stimulation element 12 (FIG. 1A) employs asynchronous nerve stimulation to achieve stable respiration despite potential sleep disordered breathing.

With the example of pattern 202 and stimulation protocol 210 as a foundation, it will be understood that in some examples, a stimulation protocol is adopted in which the duration of the stimulation period of each stimulation cycle is at least 50 percent of the duration of the reference respiratory cycle. In at least some contexts, this arrangement may ensure that the probability of entirely missing inspiration in an asynchronous stimulation protocol is less than 50%, such that a majority of the treatment period, stimulation will be delivered during at least a portion of inspiration, which may be sufficient to minimize or prevent sleep disordered breathing (e.g. apneas).

In some examples, a stimulation protocol is adopted in which the duration of the stimulation period of each stimulation cycle is 80 percent of the duration of the reference respiratory cycle. For instance, such an arrangement might be employed in some example patients having severe obstructive sleep apnea in which an inspiration can be missed for no more than 1 of 5 breaths. When applied asynchronously, such a duty cycle may likely ensure effective treatment (assuming other stimulation parameters are effective) while still allowing the protrusor muscles to rest sufficiently.

While not depicted in FIG. 3B, in some examples, a stimulation protocol is adopted in which the duration of the stimulation period of each stimulation cycle is at least 25 percent of the duration of the reference respiratory cycle. When employed in an asynchronous arrangement, such an arrangement will likely ensure that at least one stimulation period significantly overlaps with the inspiratory phase at least one breath (e.g. one respiratory cycle) out of every three breaths (i.e. three respiratory cycles). For some patients which exhibit less severe apneas, this arrangement can be sufficient to prevent obstructive events.

FIG. 3C is a diagram 221 schematically illustrating a stimulation protocol 220 implemented via independent stimulation function 14 (FIG. 1A), according to one example of the present disclosure. In one example, diagram 221 includes at least some of substantially the same features and attributes as diagram 201, except for having a different stimulation protocol 220.

Moreover, as represented by the legend 229, the stimulation protocol 220 operates according to a stimulation cycle in which the duration of the stimulation cycle is greater than the duration (R) of the reference respiratory cycle. In some examples, the duration of the stimulation period exceeds the duration of the non-stimulation period by a factor of at least 1.5. As represented via legend 229, in some examples stimulation protocol 220 includes a stimulation cycle including a stimulation period of 4½ time units and a non-stimulation period of 2½ time units, with the overall stimulation cycle of 7 time units having a duration greater than the duration R of the respiratory cycle (e.g. 204A) of 6 time units.

In a manner substantially the same as previously noted for stimulation protocol 210, even though stimulation protocol 220 is not synchronized relative to a characteristic (e.g. inspiration) of the respiratory waveform, no matter where the stimulation protocol 220 is started relative to a series of respiratory cycles, the stimulation periods will overlap with at least a portion of the inspiratory phase of the respective reference respiratory cycles for a significant majority of the treatment period. For instance, even if the stimulation protocol happens to be initiated at a time that the non-stimulation period 228B generally coincides with the inspiratory phase 162 of a respiratory cycle 204C, the succeeding stimulation period 222C at least partially overlaps the inspiratory phase 162 of the next respiratory cycle 204D, and with later successive stimulation periods significantly overlapping (e.g. stimulation period 222D, exhibiting at least a majority overlap) or completely overlapping (e.g. stimulation period 222E) the inspiratory phase 162 of the respective successive respiratory cycles (e.g. 204E, 204F).

In some examples, a stimulation protocol is applied in which a total duration of stimulation via the first stimulation protocol during a treatment period is greater than 30 percent of the total duration of the treatment period.

In one aspect, in stimulation protocol 220 the duration of each stimulation period (e.g. 222A-222G) is less than a duration (R) of the respiratory cycles 204A-204H) but greater than a duration of the inspiratory phase 162 of an individual respiratory cycle (e.g. 204A).

In one aspect, a duty cycle exhibited by the repeating stimulation cycle varies on a respiratory cycle-by-respiratory cycle basis. For instance, during respiratory cycles 204D, 204E, 204F, 204G the stimulation duty cycle is 3½ time units of continuous stimulation and 2½ time units of non-stimulation, which equals about 58%. However, during respiratory cycles 204A and 204B the stimulation duty cycle is 4½ time units of continuous stimulation and 1½ time units of non-stimulation, which equals about 75%. Meanwhile, during respiratory cycles 204C, the duty cycle is 4 time units of continuous stimulation and 2 time units of non-stimulation, which equals about 67%. Every 8 respiratory cycles, the series of stimulation cycles repeats itself, as illustrated at respiratory cycle 204H, at which the first end 224 of the stimulation period 222G once again coincides with the beginning of the inspiratory phase 162 of the respiratory cycle 204H in a manner similar to respiratory cycle 204A. Accordingly, in one aspect, the long term or average duty cycle over a long period of time is about 64%.

In some examples, via stimulation protocol 220 no more than four respiratory cycles occur without a stimulation period significantly overlapping (e.g. at least a majority of the) inspiratory phase 162 of respiratory cycles in FIG. 3C.

FIG. 3D is a diagram 231 schematically illustrating a stimulation protocol 230 implemented via independent stimulation function 14 (FIG. 1A), according to one example of the present disclosure. In one example, diagram 231 includes at least some of substantially the same features and attributes as diagram 201 (FIG. 3B) or diagram 221 (FIG. 3C), except for having a different stimulation protocol 230.

Moreover, as represented by the legend 239, the stimulation protocol 220 operates according to a stimulation cycle in which the duration of the stimulation cycle is greater than the duration (R) of the reference respiratory cycle. In some examples, the duration of the stimulation period exceeds the duration of the non-stimulation period by a factor of at least 3. As represented via legend 239 in FIG. 3D, in some examples stimulation protocol 230 includes a stimulation cycle including a continuous stimulation period of 7½ time units and a non-stimulation period of 2½ time units, with the overall stimulation cycle of 10 time units having a duration greater than the duration R of the respiratory cycle (e.g. 204A) of 6 time units.

In a manner substantially the same as previously noted for stimulation protocols 210, 220, even though stimulation protocol 230 is not synchronized relative to a characteristic (e.g. inspiration) of the respiratory waveform, no matter where the stimulation protocol 230 is started relative to a series of respiratory cycles, the stimulation periods will overlap with at least a portion of the inspiratory phase of the respective respiratory cycles for a significant majority of the treatment period. Accordingly, even if the stimulation protocol happens to be initiated at a time that the non-stimulation period 238B generally coincides with the inspiratory phase 162 of a respiratory cycle 204D, the succeeding stimulation period 232C at least partially overlaps the inspiratory phase 162 of the next respiratory cycle 204E.

In one aspect, in stimulation protocol 230 the duration of each stimulation period (e.g. 232A-232D) is greater than a duration (R) of the respiratory cycles 204A-204G) and greater than a duration of the inspiratory phase 162 of an individual respiratory cycle (e.g. 204A).

In one aspect, a duty cycle exhibited by the repeating stimulation cycle varies on a respiratory cycle-by-respiratory cycle basis. For instance, during respiratory cycle 204A, the duty cycle is 6 time units of continuous stimulation, which equals 100%. However, during respiratory cycles 204B and 204E the stimulation duty cycle is 3½ time units of continuous stimulation and 2½ time units of non-stimulation, which equals about 58%. Meanwhile, during respiratory cycle 204C, the duty cycle is 5½ time units of continuous stimulation and ½ time units of non-stimulation, which equals about 92 percent. Meanwhile, during respiratory cycle 204D, the duty cycle is 4 time units of continuous stimulation and 2 time units of non-stimulation, which equals about 66 percent.

Every 5 respiratory cycles, the series of stimulation cycles repeats itself, as illustrated at respiratory cycle 204F, at which the first end 234 of the stimulation period 232D once again coincides with the beginning of the inspiratory phase 162 of the respiratory cycle 204F in a manner similar to respiratory cycle 204A.

In one aspect, the long term (i.e. average) duty cycle over a sufficient number of respiratory cycles is about 75 percent.

In one aspect, this stimulation protocol provides an occasional 100% duty cycle (e.g. stimulation period 232D) to ensure that an inspiratory phase will be not missed during a stimulation period, while the overall average duty cycle is 75 percent. In some examples, such stimulation protocols are suitable for a patient in which the pattern of the respiratory waveform varies considerably but where effective therapy can be achieved without using continuous stimulation.

In some examples via stimulation protocol 230 no sequence of four respiratory cycles occurs without a stimulation period at least significantly overlapping the inspiratory phase 162 of respiratory cycles in FIG. 3D.

Figure 3E:
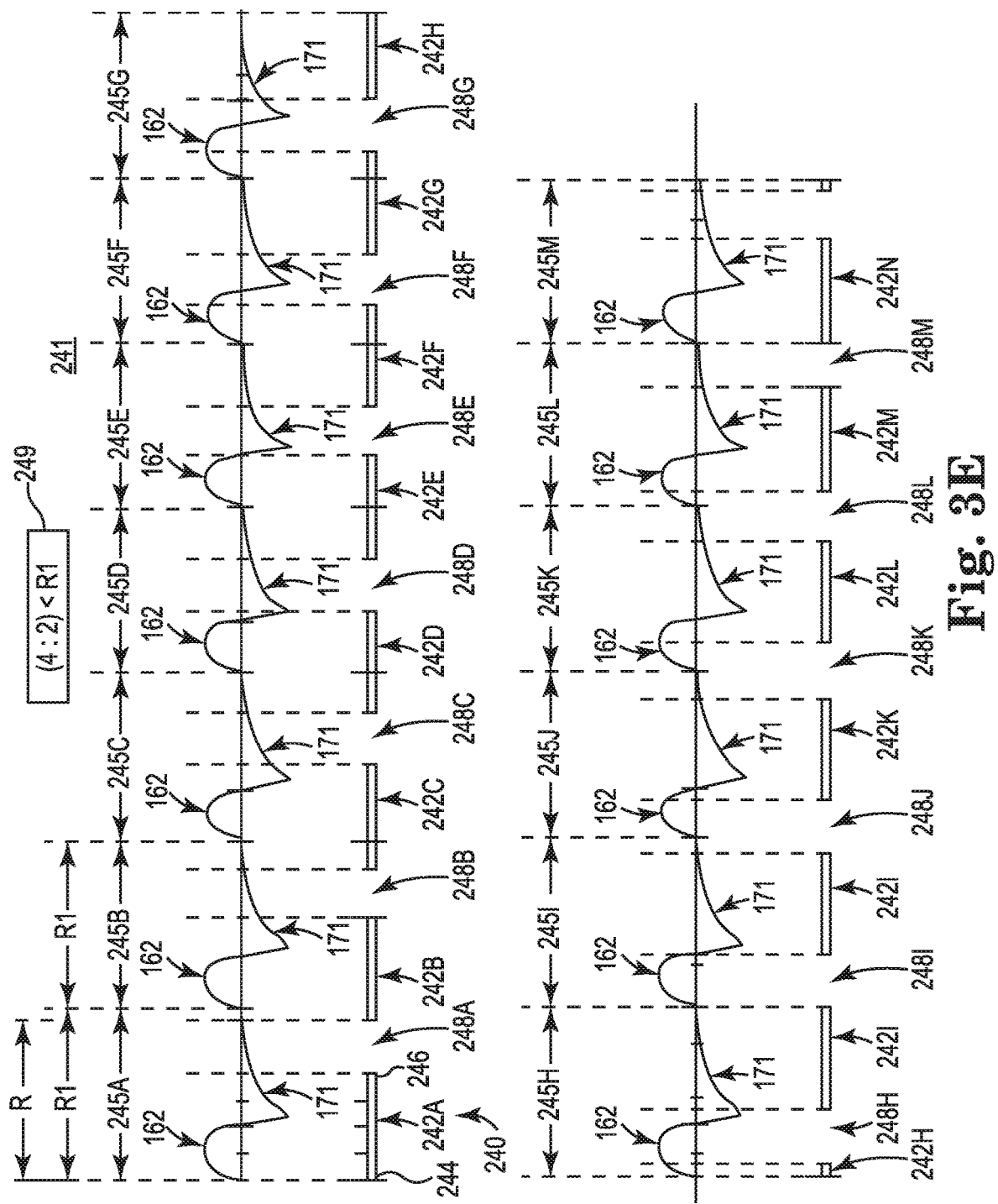
FIG. 3E is a diagram schematically illustrating a series of reference respiratory cycles juxtaposed relative to a stimulation protocol, according to one example of the present disclosure.

FIG. 3E is a diagram 241 schematically illustrating a stimulation protocol 240 implemented via independent stimulation function 14 (FIG. 1A), according to one example of the present disclosure. In one example, diagram 241 includes at least some of substantially the same features and attributes as diagram 201, except for having a different stimulation protocol 240.

As represented via legend 249 in FIG. 3E, stimulation protocol 240 includes a stimulation cycle including a continuous stimulation period of 4 time units and a non-stimulation period of 2 time units, with the overall stimulation cycle of 6 time units having a duration generally matching the duration R of the reference respiratory cycle (e.g. 204A) of 6 time units. As in the prior examples associated with FIGS. 3A-3E, the stimulation protocol 240 is independent, i.e. not synchronized relative to sensing of respiratory information.

In some patients the duration (R) of their respiratory cycle may vary slightly over time as the respiratory cycle might shorten or lengthen. Diagram 241 schematically illustrates just one example in which the reference respiratory cycle represents a situation in which the duration of the respiratory cycle lengthens to R1 due to lengthening of the expiratory phase 171 of the respiratory cycles of the patient. It will be understood that other characteristics, parameters, features of the respiratory cycle often change as well, but these changes are not depicted in FIG. 3E for illustrative simplicity and clarity.

It will be further understood that such changes may develop gradually over time and that FIG. 3E provides a snapshot of one such change after it has already at least partially developed. Moreover, because this arrangement of independent stimulation operates without synchronization relative to sensed respiratory information, FIG. 3E schematically represents at least some aspects regarding how stimulation protocol 240 may provide therapeutic effectiveness in this situation of lengthening respiratory cycles (or shortened respiratory cycles) as represented by the reference respiratory cycles 204A-245M in FIG. 3E.

Accordingly, in this example, the stimulation cycle repeats itself in what otherwise would be exactly matching each reference respiratory cycle, but the elongated duration of the reference respiratory cycle causes the stimulation cycle to no longer coincide with various portions of the respiratory cycle.

It will be understood, of course, as previously noted elsewhere that at the time the stimulation protocol is initiated and while not shown in FIG. 3E, the first end 244 of the initial stimulation period 242A may not necessarily coincide with the beginning of an inspiratory phase 162 of a respiratory cycle 245A.

In some examples, even though stimulation protocol 240 is not synchronized relative to a characteristic (e.g. inspiration) of the respiratory waveform, no matter where the stimulation protocol 240 is started relative to a series of respiratory cycles, the stimulation periods will overlap with at least a portion of the inspiratory phase of the respective respiratory cycles for a significant majority of the treatment period. Accordingly, even if the stimulation protocol happens to be initiated at a time that the non-stimulation period 248H 248I, 248J generally coincides with the inspiratory phase 162 of a respiratory cycle 245H, 245I, 245J, at least some subsequent stimulation periods 242L, 242M, 242N significantly overlap (at least a majority overlap) the inspiratory phase 162 of the next respiratory cycles 245K, 245L, 245M. As further seen in FIG. 3E, other example stimulation periods also significantly overlap (e.g. stimulation period 242F) the inspiratory phase 162 of the corresponding respective respiratory cycle 245F.

In some examples, the stimulation periods 242A-242E, 242N completely overlap the inspiratory phase 162 of the respective respiratory cycles (e.g. 245A-245E, 245M). However, it will be understood that in some examples, such complete overlap with the inspiratory phase of some respiratory cycles may not be exhibited, and a significant overlap would suffice to achieve adequate airway patency.

In one aspect, in stimulation protocol 240, the duration of each stimulation period (e.g. 242A-242M) is less than a duration (R) of the respiratory cycles (245A-245M) but greater than a duration of the inspiratory phase 162 of an individual respiratory cycle (e.g. 245A).

In one aspect, the duty cycle associated with the stimulation cycle varies on a respiratory cycle-by-respiratory cycle basis. For instance, during respiratory cycles 245A, 245B, 245C, 245D, 245E, 245F, 245G, 245H, 245M the duty cycle is 4½ time units of continuous stimulation and 2 time units of non-stimulation, which equals about 75 percent. However, during respiratory cycles 245I, 245J, 245K, 245L the duty cycle is 4 time units of continuous stimulation and 2½ time units of non-stimulation, which equals about 62 percent.

For at least the time that a particular duration (R1) of the elongated respiratory cycle persists (as represented by reference respiratory cycles), every 12 respiratory cycles, the series of stimulation cycles repeats itself, as illustrated at respiratory cycle 245M, at which the first end 244 of the stimulation period 242N once again coincides with the beginning of the inspiratory phase 162 of the respiratory cycle 245M in a manner similar to respiratory cycle 245A.

In one aspect, the long term, average stimulation duty cycle over a sufficient period of time is about 67 percent.

Accordingly, in some examples, via stimulation protocol 240 no sequence of four respiratory cycles occurs without a stimulation period at least partially overlapping or even significantly overlapping the inspiratory phase 162 of respiratory cycles in FIG. 3E.

It will be further understood that the various stimulation protocols described and illustrated in association with at least FIGS. 3B-3E are implemented via the at least partially implantable stimulation system 20 as described in association with at least FIGS. 1-14. However, in some examples, the various stimulation protocols described and illustrated in association with at least FIGS. 3B-3E are implemented via at least some components, elements, systems etc. other than those described in association with FIGS. 1-14.

While the independent stimulation function 14 (FIG. 1A) does not use sensed respiratory information to trigger each stimulation period or synchronize each stimulation period, in some examples the independent stimulation mode 14 uses sensed respiratory information to track how a stimulation protocol is matching up relative to the characteristics of the sensed respiratory waveform. Accordingly, upon elongation or shortening of the sensed respiratory cycles, the therapy manager 16 (including independent stimulation function 14) can choose to maintain or modify which stimulation protocol is being applied in order to ensure that the desired amount and timing of stimulation is being applied. In addition, or as an alternative, the therapy manager 16 uses the sensed respiratory information to adjust or calibrate features of the reference respiratory cycle associated with a particular stimulation protocol.

In some examples, operation of the therapy manager 16 (as part of an at least partially implantable stimulation system 20) is not limited to the specific stimulation protocols described in association with at least FIGS. 3B-3E, as other stimulation protocols can be implemented with longer or shorter stimulation periods and with longer or shorter non-stimulation periods.

Figure 16A:
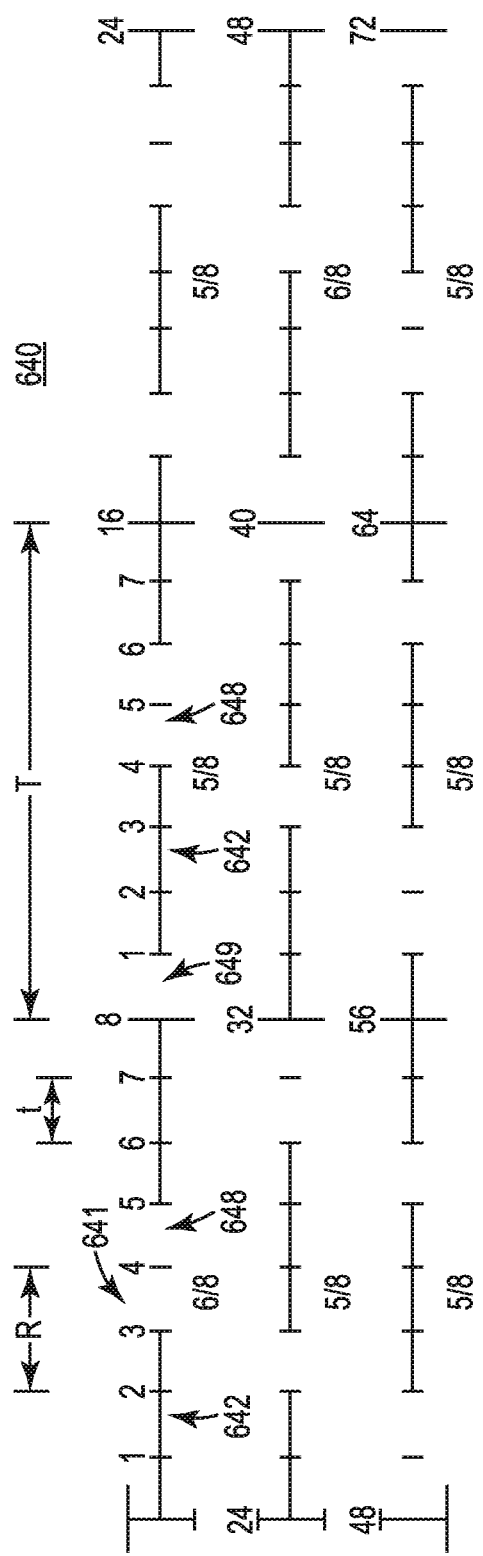
FIG. 16A is a diagram schematically illustrating a stimulation protocol, according to one example of the present disclosure.

In some examples the independent stimulation function 14 (FIG. 1A) includes a complex stimulation cycle in which at least two different length stimulation periods is employed and/or at least two different length non-stimulation periods is employed. As one non-limiting example to illustrate the principle, one stimulation protocol could include a first continuous stimulation period of three time units, a first non-stimulation period of two time units, a second continuous stimulation period of three time units, followed by a second non-stimulation period of one time unit. The example later described in association with FIG. 16A illustrate some aspects of these features.

In some examples, and as illustrated in the diagrams of FIGS. 3B-3E, the stimulation cycles are not centered relative to a characteristic or feature of a respiratory waveform. In other words, the respective continuous stimulation periods or non-stimulation periods (in the example stimulation protocols) are not fixed or tied to a particular landmark or fiducial of the respiratory waveform. Accordingly, the respective continuous stimulation periods and non-stimulation periods within stimulation cycles (of a particular stimulation protocol) vary regarding which portion of a respiratory cycle (of a series of respiratory cycles) with which they coincide.

In some examples, the independent stimulation function 14 provides a stimulation protocol having a duty cycle of 80 percent, where a 100 percent duty cycle would correspond to continuous stimulation over a full respiratory cycle. In one example, a first portion of the duty cycle comprises a continuous stimulation period and a second portion of the duty cycle comprises a continuous non-stimulation period immediately following the first portion. In a non-limiting example in which a respiratory cycle has a duration of 5 seconds, the duty cycle includes applying continuous stimulation for 4 seconds immediately followed by continuous non-stimulation for 1 second, with the duty cycle being repeated.

FIG. 4 is a block diagram 251 schematically illustrating a plurality of stimulation parameters 250, according to one example of the present disclosure. In general terms, these stimulation parameters may be employed as part of implementing one of the stimulation protocols described in association with FIGS. 3B-3E and/or as part of general operation of stimulation element 12 (FIG. 1A) and/or therapy manager 16 (FIG. 1B). In one example, a single parameter is implemented, while in some examples, several of these parameters may be implemented. When several parameters are implemented, they are implemented separately but contemporaneously in some examples and in other examples, they are implemented in combination.

As shown in FIG. 4, these stimulation parameters 250 include amplitude parameter 252, a duty cycle parameter 254, a respiratory cycle duration parameter 260, a time unit parameter 262, and a time frame parameter 270. The amplitude parameter 252 controls an amplitude of the stimulation signal, which can be selected for a particular stimulation protocol.

In some examples, the duty cycle parameter 254 tracks and/or controls a duty cycle of stimulation. In some examples, the stimulation duty cycle is expressed relative to a duration (R) of one respiratory cycle (per parameter 260) in the manner previously described regarding the stimulations protocols previously described in association with at least FIGS. 3B-3E. The duty cycle parameter 254 comprises a constant function 256 and a variable function 258. The constant function 256 implements a duty cycle in which the stimulation duty cycle is identical relative to each respiratory cycle, while the variable function 258 implements a duty cycle in which the stimulation duty cycle varies relative to at least some respiratory cycles within a series of respiratory cycles.

As previously described in association with at least FIGS. 3B-3E, in some examples, the stimulation duty cycle is implemented according to a series of stimulation cycles in which each stimulation cycle includes at least one continuous stimulation period and at least one non-stimulation period. At least some stimulation protocols includes stimulation cycles in which the duration of the stimulation period(s) differs relative to the duration of the non-stimulation period(s) through a series of stimulation cycles such that an average duty cycle can be calculated.

Accordingly, the various stimulation protocols provide some duty cycles that vary from one respiratory cycle to the next, while simultaneously providing an overall or average duty cycle. By selecting a particular stimulation cycle, specific duty cycles are implemented on a respiratory-cycle by respiratory-cycle basis and an overall or average duty cycle is achieved.

In some examples, a respiratory cycle duration parameter 260 identifies a duration of a patient-specific average respiratory cycle during reasonably stable respiration (e.g. normal breathing) or a duration of a multi-patient average respiratory cycle during reasonably stable respiration. In some examples, the patient-specific average respiratory cycle is determined according to recent sensed respiration information while in some examples, the patient-specific average respiratory cycle is determined according to long term data gathered for that patient during reasonably stable respiration (e.g. normal breathing).

In some examples, the respiratory cycle duration parameter 260 tracks a duration of the sensed respiratory cycles of a patient and determines an average.

In some examples, the time unit parameter 262 tracks and controls a number of time units by which a stimulation cycle operates. In some examples, the time unit parameter 262 implements time units as a multiple of some natural time unit associated with a respiratory waveform. For instance, in some examples such as the stimulation protocols described and illustrated in association with FIGS. 3B-3E, the time unit parameter 262 equates six time units with a duration of a respiratory cycle, and in which an inspiratory phase comprises one-third of the entire respiratory cycle. However, it will be understood that in some examples, the time units (per parameter 262) are unit-less. For instance, suppose the respiratory period has a duration R of five seconds, and a convention has been adopted that the respiratory cycle is divisible into six time units. Then, the six time units would be distributed across the five second duration of the respiratory cycle.

In some examples, the time unit parameter 262 implements time units which are entirely arbitrary relative to one or more natural time units associated with a respiratory waveform. For instance, in some examples such as the stimulation protocol described and illustrated in association with FIG. 16A, the time unit parameter 262 equates eight time units with a duration of a respiratory cycle, and in which an inspiratory phase comprises one-third of the entire respiratory cycle.

In some examples, the time frame parameter 270 in FIG. 4 identifies a respiratory cycle series parameter 272 and a stimulation cycle parameter 274. The respiratory cycle series parameter 272 identifies and tracks the number of respiratory cycles that occur before a particular portion of a particular stimulation cycle (274) would coincide again with a particular portion of a respiratory cycle. For example, it was previously noted in association with at least FIG. 3C that the stimulation protocol 220 operated based on a time frame of seven respiratory cycles such that a sequence of seven respiratory cycles would occur before a beginning of a stimulation period of a stimulation cycle would coincide with a beginning of an inspiratory phase of the repeating respiratory cycle. While the stimulation protocols associated with independent stimulation function 14 (FIG. 1A) are not synchronized relative to characteristics (e.g. inspiratory phase) of a sensed respiratory waveform, the time frame parameter 270 enables tracking and adjusting how a given stimulation protocol is juxtaposed relative to sensed patient respiratory behavior.

FIG. 5 is a block diagram of a stimulation protocol element 280, according to one example of the present disclosure. As shown in FIG. 5, the stimulation protocol element 280 comprises an array parameter 282, a rotation parameter 284, an automatic parameter 286, a manual parameter 288, a static parameter 290, and a custom parameter 291.

In some examples, stimulation protocol element 280 includes at least some of substantially the same features and attributes as stimulation protocol element 12, as previously described in association with at least FIGS. 1-4. In particular, as previously noted, in some examples the independent stimulation function 14 (FIG. 1A) provides at least one stimulation protocol suitable for delivering electrical stimulation to a nerve of a patient, such as one of the stimulation protocols as previously described and illustrated in association with FIGS. 3B-3E.

With this in mind, array parameter 282 of stimulation protocol element 280 provides an array of stimulation protocols that can be applied, such as but not limited to those illustrated in association with FIGS. 3B-3E.

In some examples, via a rotation parameter 284, the stimulation protocol 280 enables delivering therapeutic nerve stimulation to a patient while rotating through different stimulation protocols available via array parameter 282. In some examples, such rotation enables identifying a stimulation protocol that works best for a particular patient on a particular day or on a long term basis. However, in some examples, rotation through different stimulation protocols is maintained for a particular day or on a long term basis to provide a large degree of variability in the overall stimulation pattern to thereby provide a robust therapy regimen when a patient's respiratory behavior is consistently erratic and/or when sensing of a patient's respiratory behavior is consistently problematic.

In some examples, in cooperation with an automatic parameter 286, the rotation parameter 284 automatically rotates through the different stimulation protocols to achieve goals set by therapy manager 16 (FIG. 1B). In some examples, via automatic parameter 286, the therapy manager 16 (FIG. 1B) automatically selects at least one stimulation protocol suitable for a particular patient. In some examples, the automatic selection of which stimulation protocol(s) is best suited for a particular patient is based on a sensed respiratory waveform of the patient.

In some examples, via a static parameter 290 shown in FIG. 5, therapy manager 16 (FIG. 1B) enables selecting and then maintaining a single stimulation protocol indefinitely until and unless a user or operator selects a different stimulation protocol or parameters affecting the selected stimulation protocol. In some examples, if a particularly effective stimulation protocol is identified during operation of the rotation parameter 284, the therapy manager 16 (FIG. 1B) deactivates automatic rotation of the stimulation protocols and operates that single, "particularly effective" stimulation protocol, per the static parameter 290.

In some examples, stimulation protocol element 280 includes custom parameter 291, which enables adjusting a selected stimulation protocol or making a custom stimulation protocol by selecting a duration of respiratory cycle, duration of stimulation period(s), duration of non-stimulation periods, duration of stimulation cycle, and/or other parameters identified in the plurality of stimulation parameters 250 (FIG. 4).

In some examples, the range of stimulation protocols available to a patient via stimulation protocol element 280 are selected and/or bounded according to the discretion of a physician or physician programmer.

FIG. 6 is a block diagram of a power element 320, according to one example of the present disclosure. In one example, power element 320 represents IPG 35, 50 (FIGS. 2A-2B) as having an external power source 322 and/or an on-board power source 324.

In some examples, an at least partially implantable stimulation system (according to examples of the present disclosure) operates in cooperation with and/or incorporates sensing functionality. With this in mind, in some examples, such systems include a sensing element 330, according to one example of the present disclosure, as shown in FIG. 7A. The sensing element receives and/or obtains respiratory information.

In some examples, the sensing element 330 includes an on-board sensing element 332, which is physically incorporated into IPG 35 (FIG. 2A) or IPG 50 (FIG. 2B) in some manner such that communication between the on-board sensing element 332 and other elements of the IPG 35, 50 will occur within the case or housing of the IPG. In some examples, the on-board sensing element 332 includes internal components, such as an accelerometer and in some examples, the on-board sensing element 332 includes surface components, such as the external surface of the case or housing of the IPG 35, 50 acting as a sensing element alone or in combination with other sensing elements.

In some examples, the sensing element 330 includes an implanted sensing input 334 to receive signals from a sensor implanted within the body physically separate from the IPG 35, 50, with the sensing input 334 in communication with and/or connected to the IPG 35, 50 via wired or wireless communication pathways.

In some examples, the sensing element 330 includes an external sensing input 336 to receive signals from a sensor external to the patient's body, with the sensing input 336 in communication with the IPG 35, 50 via wireless communication pathways.

In some examples, sensing element 330 does not comprise a physically-embodied sensor but rather a sensing input to receive information sensed via sensors separate from, and independent of, sensing element 330 with such sensors in communication with sensing element 330.

In some examples, sensing element 330 can comprise both a sensing input and a physically-embodied sensor.

Via these various sensing elements and inputs, the sensing element 330 receives and tracks signals from at least one physiologic sensor in order to gather information pertinent to treating sleep disordered breathing. In some examples, this information includes respiratory information such as, but not limited to, determining a respiratory state of a patient, whether or not the patient is asleep or awake, and other respiratory-associated indicators, etc. In some examples, the type of sensed physiologic information received by, and/or the type of physiologic sensors embodied within, one of the sensing elements/inputs 332, 334, 336 (FIG. 7A) include, but are not limited to, a pressure sensing, blood oxygenation sensing, acoustic sensing, posture sensing, motion/activity sensing, differential pressure sensing, electrocardiogram (ECG) sensing, or impedance sensing. Via such sensing modalities, the system can measure thoracic impedance, respiratory pressure, diaphragm-based parameters, electrocardiac monitoring, airflow monitoring, snoring, etc. Gathering of this respiratory information, including information regarding respiratory-related behaviors, may be implemented via either a single sensor or any combination of various physiologic sensors that can provide a reliable and accurate signal. In some examples, these various measures of respiratory-related behavior can be considered alone or together in combination to indicate respiratory effort, which is at least one type of respiratory information receivable and/or obtainable by the sensing element.

In some examples, the therapy manager 16 (FIG. 1B) maintains the sensing components of the sensing element 330 in a default, dormant mode (i.e. off or low power) and periodically activates one or more of the available sensing element(s) to gather patient data. After gathering the data, the sensing elements are deactivated, thereby resuming their dormant mode. In some examples, the gathered patient data is used to evaluate the effectiveness of the therapy, such as the number, intensity, and/or frequency of apneas occurring. After such data gathering, the therapy manager 16 (FIG. 1B) deactivates the sensing element(s), thereby returning them to a dormant mode.

In some examples, the gathered patient data is used to measure the respiratory period to verify its duration and to determine or verify the relative durations (or absolute duration) of the inspiratory and expiratory phases. This information is used to assess a current stimulation protocol and potentially determine whether adjustments to the stimulation protocol are warranted or whether a different stimulation protocol should be employed. For instance, in some examples, the gathered patient data from the temporarily activated sensing elements is used to calibrate the reference respiratory cycle associated with implementation of a particular stimulation protocol.

FIG. 7B is a schematic diagram of an at least partially implantable stimulation system 340, according to an example of the present disclosure. In one example, the system 340 includes at least some of substantially the same features and attributes as system 20 (previously described in association with at least FIG. 2A), except further including sensing functionality via at least one sensing element to sense respiratory information. In some examples, this sensing functionality is implemented via sensing element 330 (FIG. 7A).

In some examples, the system 340 comprises an additional lead 137 including at least one sensor portion 341 (electrically coupled to the IPG 35 and extending from the IPG 35) positioned in the patient 22 for sensing respiratory information, such as respiratory effort, respiratory pressure, etc. In some examples, this information includes identifying and tracking characteristics and parameters of sensed respiratory waveforms.

In some examples, the sensor portion 341 is a pressure sensor. In one example, the pressure sensor detects pressure in the thorax of the patient. In some examples, the sensed pressure could be a combination of thoracic pressure and cardiac pressure (e.g., blood flow). Via sensor portion 341, therapy manager 16 (FIG. 1B) is configured to analyze this pressure sensing information to identify, track, and evaluate the respiratory patterns of the patient.

In some examples, the respiratory sensor portion 341 comprises a bio-impedance sensor or forms one of a pair of bio-impedance sensors. In some examples, the respiratory sensor portion 341 is located in regions other than the pectoral region. In some examples, the sensor portion 341 is used to sense impedance in cooperation with other electrodes (e.g. a stimulation electrode) or with an electrically conductive exterior housing of the IPG 35, 50 (FIGS. 2A-2B, 7B). In some examples, as shown in FIG. 7B, additional sensors 347, 348, 349 are distributed about the chest area for measuring a trans-thoracic bio-impedance signal, an electrocardiogram (ECG) signal, or other respiratory-associated signals. In some examples, sensor portion 341 is omitted and sensors 347, 348, 349 are implemented.

In some examples, the system 340 for treating obstructive sleep apnea is a totally implantable system which provides therapeutic solutions for patients diagnosed with obstructive sleep apnea. However, as identified in various examples, in some examples, the system is partially implantable with some components (e.g. power source, sensing elements, or control circuitry) being at least partially or completely external to the patient's body.

In some examples, the previously-described at least partially implantable system 80 (FIG. 2D) includes at least some of substantially the same features described and illustrated in association with FIGS. 4-7B, except for system 80 having a non-pectoral location and those attributes specific to system 80 as described in association with FIG. 2D.

In some examples, the respiratory information and/or other physiologic information gathered via the sensing element 330 (FIG. 7A) and associated sensor schemes (FIG. 7B) is used to identify, track, evaluate, etc. various therapeutic parameters. Accordingly, in some examples the at least partially implantable stimulation system includes a therapeutic monitoring element 350, which as shown in FIG. 8, includes a plurality of therapeutic parameters. In some examples, these parameters include identifying, tracking, and evaluating apnea events per parameter 352 and/or computing and tracking an apnea severity index 354, such as AHI or other index. The index parameter 354 determines a frequency, intensity, duration, etc. of detected apneas to indicate the relative severity of sleep disordered breathing for the patient.

In some examples, one therapeutic parameter of monitoring element 350 includes a minute ventilation parameter 356 to track minute ventilation of the patient before, during, or after a therapy regimen. In some examples, one therapeutic parameter of monitoring element 350 includes a tidal volume parameter 357 to track the tidal volume of a patient before, during, or after a therapy regimen.

In some examples, one therapeutic parameter of monitoring element 350 includes a body position parameter 358. In some examples, one therapeutic parameter of monitoring element 350 includes a posture parameter 359. Together or separately, the body position parameter 358 and posture parameter 359 determine and track a body position of the patient and posture of the patient. Among other uses, such information can be used to activate or deactivate a therapy, to select a therapeutic regimen (e.g. stimulation protocol), and/or to adjust a therapeutic regimen. It will be understood that these example parameters are not exhaustive and can be employed separately from each other or in various combinations.

In some examples, this information obtained via any one or several parameters 352, 354, 356, 357, 358, 359 of the therapeutic monitoring element 350 is used to initiate, terminate, select, and/or adjust stimulation applied via the IPG 35, 50 and stimulation electrode 45. For instance, upon determining that the number and/or intensity of apneic events has met or exceeded a severity threshold, the therapy manager 16 (FIG. 1B) can utilize control portion 56 (FIG. 2C) to initiate application of stimulation to the airway-patency related nerves to open the airway and thereby reduce the associated sleep disordered breathing behavior. However, it will be understood that in at least some examples, this arrangement does not include causing (or depend on) the stimulation signal to become synchronized relative to a characteristic (e.g. inspiratory phase, expiratory phase, etc.) of the respiratory waveform. Rather, as noted in association with at least FIG. 1A, in the examples described thus far in association with FIGS. 1-8, such stimulation is applied independent of such synchronization.

In some examples, the therapeutic parameters element 350 may be employed to select one of a plurality of stimulation protocols and/or to evaluate the therapeutic effectiveness of a particular stimulation protocol(s) for a particular patient for a given period of time or on a long term basis.

In at least this context and/or other contexts in at least some examples of the present disclosure, therapeutic effectiveness may correspond to alleviating sleep disordered breathing, which in some instances is measurable via a severity threshold, such as an apnea-hypopnea index (AHI) and/or other scoring mechanisms. In some examples, the therapeutic effectiveness may also be measured or evaluated relative to sensor signal quality, such as via sensor signal quality criteria as described in at least some of the examples of the present disclosure.

FIG. 9 is a block diagram schematically illustrating a control portion 360, according to one example of the present disclosure. In some examples, control portion 360 includes a controller 362 and memory 370. In some examples, therapy manager 371 is stored in memory 370, and in some examples, therapy manager 371 includes at least some of substantially the same features and attributes as therapy manager 16 (FIG. 1B), as previously described in association with at least FIGS. 1-8.

In general terms, controller 362 of control portion 360 comprises at least one processor 364 and associated memories that are in communication with memory 370 to generate control signals to direct operation of at least some components of the systems and components described throughout the present disclosure. In some examples, these generated control signals include, but are not limited to, employing therapy manager 371 to manage operation of the stimulation system to control sleep disordered breathing. In some examples, a control portion 360 is present in the IPG 35, 50, 84 (FIGS. 2A, 2B, 2D) as control portion 56 (FIG. 2C) and/or is accessible to the IPG 35, 50, 84. In some examples, at least some aspects of stimulation element 12 (FIG. 1A) are at least partially implemented via control portion 360 and/or in communication with control portion 360, with at least some aspects of stimulation element 12 being storable in memory 370 with or as part of therapy manager 371.

In particular, in response to or based upon commands received via a user interface 396, 400 (FIGS. 11A, 11B) and/or machine readable instructions (including software), controller 362 generates control signals to implement a nerve stimulation protocol to control sleep disordered breathing, in accordance with at least some of the previously described examples and/or later described examples of the present disclosure. In some examples, controller 362 is embodied in a general purpose computer while in other examples, controller 362 is embodied in at least some of the components described throughout the present disclosure, such as IPG 35, 50, 84 or external components operatively coupled to implantable pulse generator 35, 50, 84. For purposes of this application, in reference to the controller 362, the term "processor" shall mean a presently developed or future developed processor (or processing resources) that executes sequences of machine readable instructions contained in a memory. In some examples, execution of the sequences of machine readable instructions, such as those provided via therapy manager 371 stored in memory 370 of control portion 360, cause the processor to perform actions, such as operating controller 362 to implement stimulation protocols as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium), as represented by memory 370. In some examples, memory 370 comprises a computer readable tangible medium providing non-volatile storage of the machine readable instructions executable by a process of controller 362. In other examples, hard wired circuitry may be used in place of or in combination with machine readable instructions to implement the functions described. For example, controller 362 may be embodied as part of at least one application-specific integrated circuit (ASIC). In at least some examples, the controller 362 is not limited to any specific combination of hardware circuitry and machine readable instructions, nor limited to any particular source for the machine readable instructions executed by the controller 362.

In some examples, user interface 396 shown in FIG. 11A comprises a user interface or other display that provides for the simultaneous display, activation, and/or operation of at least some of the various components, functions, features, and of stimulation element 12 (FIG. 1A), therapy manager 16 (FIG. 1B), control portion 360 (FIG. 9), IPG 35, 50, 84 (FIGS. 2A, 2B, 2D), and related elements, as described throughout the present disclosure. In some examples, at least some portions or aspects of the user interface 396 are provided via a graphical user interface (GUI) and may include an input and a display.

In some examples, user interface 396 includes at least some of the components illustrated in user interface 400 schematically depicted in FIG. 11B.

Figure 12:
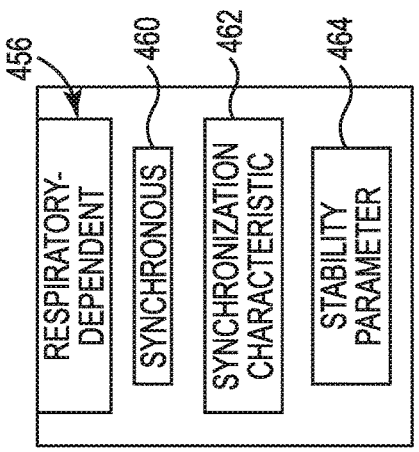
FIG. 12 is a block diagram schematically illustrating a stimulation protocol element, according to one example of the present disclosure.
Figure 15A:
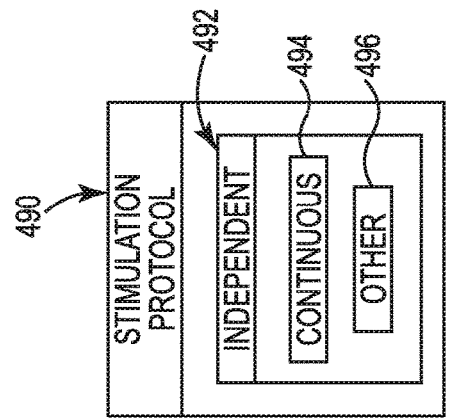
FIG. 15A is a block diagram schematically illustrating a stimulation protocol element, according to one example of the present disclosure.
Figure 14:
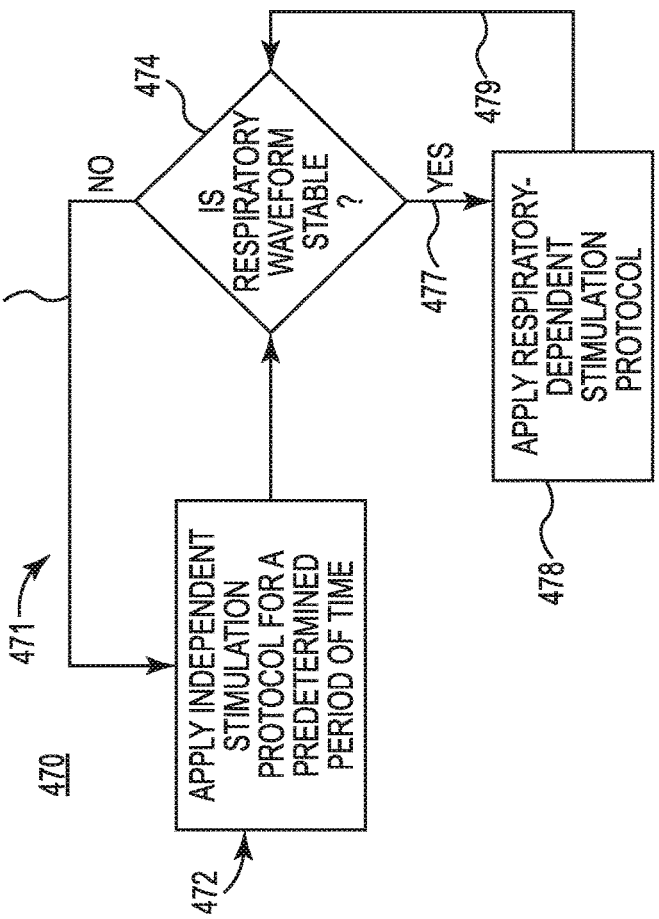
FIG. 14 is a diagram schematically illustrating at least some aspects of stimulation protocol selection, according to one example of the present disclosure.
Figure 15C:
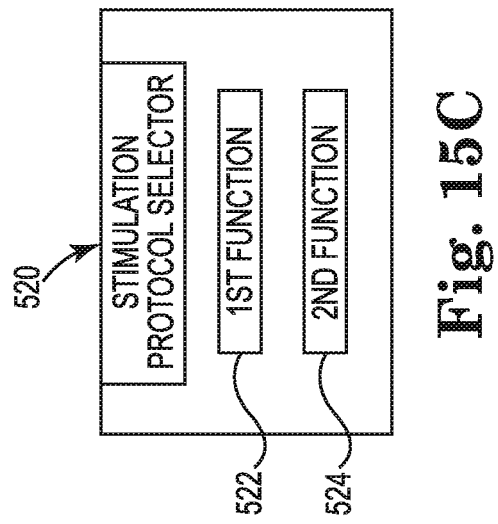
FIG. 15C is a block diagram schematically illustrating a stimulation protocol selector, according to one example of the present disclosure.
Figure 15B:
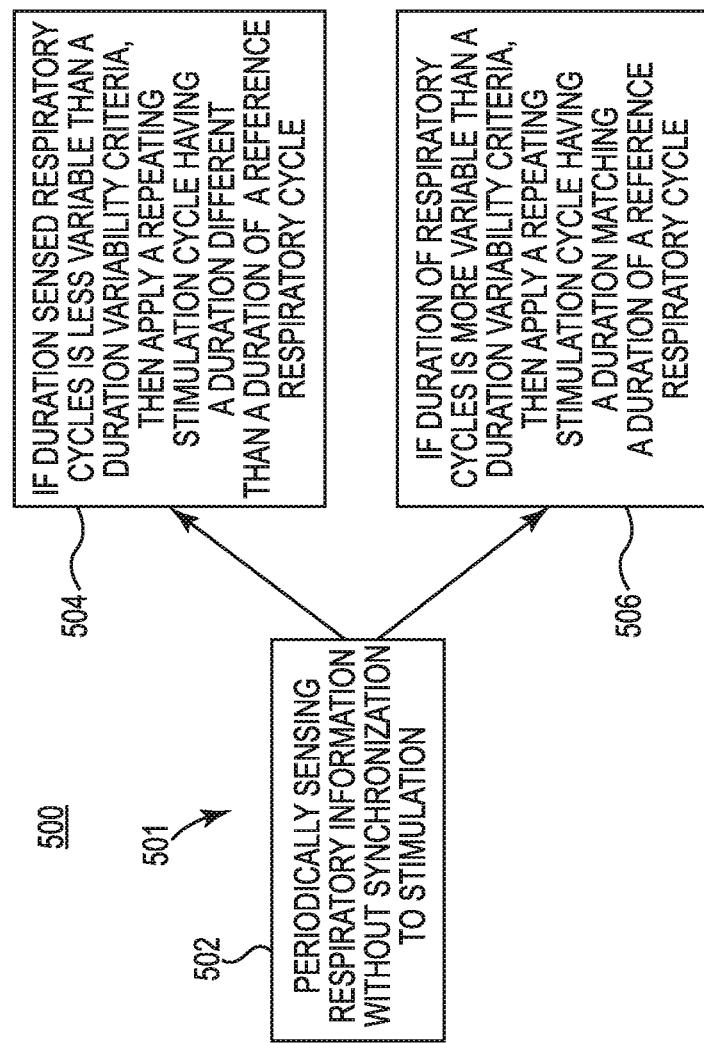
FIG. 15B is a diagram schematically illustrating at least some aspects of stimulation protocol selection, according to one example of the present disclosure.

As shown in FIG. 11B, user interface 400 includes at least some of the various components, functions, elements, and features as described and illustrated in association with at least stimulation protocol elements 280 (FIG. 5), 490 (FIG. 15A), therapeutic monitoring element 350 (FIG. 8), stimulation parameters 250 (FIG. 4), stimulation protocol element 450 (including independent function 454, respiratory-dependent function 456 in FIG. 12), automatic protocol selector 470 (FIG. 14), and stimulation protocol selection 500 (FIG. 15B).

FIG. 10 is a diagram 380 schematically illustrating a manner in which the control portion 360 is implemented, according to one example of the present disclosure. In some examples, control portion 360 is entirely implemented within or by an implantable pulse generator 385, which has at least some of substantially the same features and attributes as pulse generator (IPG) 35, 50, 84 as previously described in association with at least FIGS. 1-9. In some examples, control portion 360 is entirely implemented within or by a remote control 390 (e.g. a programmer) external to the patient's body, such as a patient control 392 and/or a physician control 394. In some examples, the control portion 360 is partially implemented in the pulse generator 385 and partially implemented in the remote control 390 (at least one of patient control 392 and physician control 394).

In some examples, in association with control portion 360, user interface (396 in FIG. 11A; 400 in FIG. 11B) is implemented in remote control 390.

FIG. 12 is a block diagram of a stimulation protocol element 450, according to one example of the present disclosure. As shown in FIG. 12, stimulation protocol element 450 includes an independent stimulation function 454 and a respiratory-dependent function 456. In some examples, the independent stimulation function 454 includes at least some of substantially the same features as independent stimulation function 14 associated with stimulation element 12 (FIG. 1A) and/or therapy manager 16 (FIG. 1B) as part of an at least partially implantable stimulation system, as previously described in association with FIGS. 1-11B. Meanwhile, FIG. 13 is a block diagram of a respiration-dependent function 456, according to one example of the present disclosure.

After describing the features and attributes associated with the respiration-dependent stimulation function 456, at least some examples regarding the relationship and relative operation of the independent stimulation function 454 and respiratory-dependent stimulation function 456 will be addressed.

Figure 13:
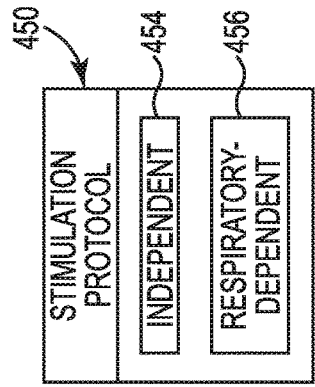
FIG. 13 is a block diagram schematically illustrating a respiratory-dependent stimulation element, according to one example of the present disclosure.

As shown in FIG. 13, in some examples, the respiratory-dependent function 456 includes a synchronous parameter 460, a synchronization characteristic parameter 462, and a stability parameter 464.

In some examples, via the synchronous parameter 460, respiratory-dependent function 456 implements a stimulation protocol in which each individual nerve stimulation period (within a treatment period) is triggered by and/or synchronized relative to a synchronization characteristic of the patient's respiratory waveform. For instance, in some examples, respiratory-dependent function 456 causes individual stimulation periods to occur substantially simultaneous with the inspiratory phase (e.g. 162 in FIG. 3B) of the patient's respiratory cycle (e.g. 204A in FIG. 3B) such that stimulation is considered to be synchronous with inspiration.

In some examples, per synchronization characteristic parameter 462, one can select (or a therapy manager can automatically select) the characteristic to which stimulation will be synchronized. In some examples, via parameter 462 respiratory-dependent stimulation function 456 causes nerve stimulation periods to be synchronized relative to a junction or transition between expiratory pause and the onset of inspiration. In some examples, via parameter 462, nerve stimulation periods are synchronized relative to a junction or transition between inspiration and the onset (i.e. beginning) of expiration. In some examples, the characteristic to which stimulation will be synchronized can be peak inspiration, peak expiration, or expiratory pause.

In some examples, stability parameter 464 of respiratory-dependent stimulation function 456 (FIG. 13) tracks and determines at least one parameter of a sensed respiratory waveform to determine the relative stability of the respiratory waveform (e.g. sensor signal quality) to provide a reliable, accurate indication of respiratory behavior to the therapy manager (371 in FIG. 9). Without a reasonably stable respiratory waveform, the respiratory-dependent function 456 cannot be implemented. In such a situation, the independent stimulation function 454 is implemented until the control portion 360 determines via stability parameter 464 that a reasonably stable respiratory waveform is available (e.g. the sensor signal has sufficient quality) and by which stimulation can be triggered and/or synchronized relative to a characteristic of the respiratory waveform.

Via the stability parameter 464, the control portion 56 of FIG. 2C (control portion 360 in FIG. 9) determines whether the respiratory waveform is stable enough (e.g. sensor signal quality is sufficient) to support synchronizing stimulation relative to characteristics (e.g. inspiratory phase) of the respiratory waveform. In some examples, the stability parameter 464 identifies and tracks parameters such as a peak-to-peak amplitude, a respiratory rate, sensor signal frequency content, signal morphology, and a duty cycle associated with at least one of inspiration, expiration, and expiratory pause, or various combinations of these parameters. In some examples, the at least one parameter comprises a statistical stability of these identified parameters. In some examples, a determination of such statistical stability may be performed relative to a known good state for the patient or a moving baseline of known good state for the patient. In some examples, a known good state corresponds to a period of respiration free from obstructive sleep apnea. In some examples, the determination of statistical stability may be performed relative to an independent threshold of statistical goodness.

In some examples, the inspiratory duty cycle is defined as the ratio of inspiration duration to the duration of respiratory period.

In some examples, the above-noted waveform signal stability or quality parameter may be evaluated after sufficient gain is applied to the signal to enable analysis. For instance, if the peak to peak amplitude is low and sensor signal quality is low, then signal gain can be increased to determine if signal quality analysis can be performed. In some examples, a sensed signal can be subject to a process in which a sensor obtains a physiologic signal, to which gain is applied prior to quality analysis, and then potentially used for synchronization of a stimulation protocol relative to the sensed respiratory waveform. In some examples, an automatic gain control mechanism is employed and queried to determine if the gain is stable so the signal may be reliably analyzed.

In some examples, via therapy manager 16, 371 (FIGS. 1B, 9), the respiratory-dependent stimulation function 456 can be disabled so that therapy is selectively applied entirely via the independent stimulation function 14 (FIG. 2A), 454 (FIG. 12). Of course, in some examples as previously described, the respiratory-dependent stimulation function 456 is not even present with the independent stimulation function 14, 454 being the sole mechanism to apply nerve stimulation.

FIG. 14 is a diagram 470 schematically illustrating a relationship between, and automatically selection between, the independent stimulation protocol 454 (FIG. 12) and the respiration-dependent stimulation protocol 456 (FIG. 12), according to one example of the present disclosure. In some examples, at least some aspects of stimulation protocol selection in diagram 470 can be embodied as a method while in some examples, at least some aspects of stimulation protocol selection in diagram 470 can be embodied as operational aspects of a stimulation protocol manager of a therapy manager, as described in association with at least FIGS. 11B-13.

In some examples, operation of the at least partially implantable stimulation system is implemented via providing cooperation or complementary deployment of the respective stimulation protocols 454, 456. In some examples, an independent stimulation protocol 454 is applied for a predetermined period of time, as shown at 472 in FIG. 14. The predetermined period of time corresponds at least to an amount of time for a stable respiration period to be established, which may be ensured based on the independent stimulation of the airway-patency-related nerve. In some examples the first predetermined period of time corresponds to a period sufficient to establish a steady state in which filtering is established, inspiration and expiration are being detected reliably, signal gain control is realized, etc.

In some examples, operation of the first independent stimulation protocol during at least the first predetermined period of time is not a test mode, such as a mode that may otherwise be dedicated to diagnosing or evaluating the operational fitness of the stimulation system. Rather, the first independent stimulation protocol operates for at least the predetermined period of time to apply therapeutic stimulation to achieve a stable respiratory behavior and a stable respiratory waveform.

In some examples, by applying stimulation protocol(s) via the independent stimulation, a stable respiratory waveform is achieved, thereby increasing the likelihood of being able to transition to operation in the respiratory-dependent stimulation at 478 than if independent stimulation at 472 were not deployed prior to the activation of the respiratory-dependent function at 478.

With further reference to FIG. 14, based on monitoring of the sensed respiratory waveform, at repeating intervals, at 474 it is queried whether the respiratory waveform is sufficiently stable to support activation of the respiratory-dependent stimulation. If the answer to the query at 474 is NO, then pathway 476 directs continued operation of independent stimulation at 472. However, if the answer to the query at 474 is YES, then pathway 477 directs initiation of operation of respiratory-dependent stimulation at 478 of FIG. 14. During operation of respiratory-dependent stimulation at 478, the query at 474 is periodically implemented via pathway 479. If the answer to the query (at 474) is NO, then operation in respiratory-dependent stimulation n (456 in FIG. 12) at 478 in FIG. 14 is terminated as operation is returned (i.e. reverts) via pathway 476 to independent stimulation at 472 in FIG. 14 for at least the predetermined period of time.

For at least the current example, it will be understood that, in the event that no stable respiratory waveform is established, the operation would remain in independent stimulation at 472 without converting to operation in respiratory-dependent stimulation 478.

In some examples, the query at 474 is performed generally continuously by monitoring parameters indicative of respiratory signal sensing quality (i.e. sensor signal quality criteria), such as but not limited to, peak to peak amplitude, inspiratory duty cycle, respiratory rate, etc. Upon one or more of these parameters failing to meet the sensor signal quality criteria, then the answer to the query (at 474) would be registered as NO. Upon meeting the sensor signal quality criteria, the answer to the query at 474 is YES.

In some examples, meeting the signal quality criteria (e.g. answer to query is YES) can be defined via a first parameter as an average peak-to-peak respiratory amplitude above a threshold, where the average is computed from the previous two respiratory cycles. In some examples, meeting the signal quality criteria (e.g. answer to query is YES) can be defined via a second parameter as a peak-to-peak respiratory amplitude variability below a threshold, where the threshold is referenced to an average computed over the previous 60 seconds. In some examples, meeting the signal quality criteria (e.g. answer to query is YES) can be defined via a third parameter as a respiratory duration variability below a threshold, where threshold is reference to an average computed of the previous 60 seconds. In some examples, meeting the signal quality criteria (e.g. answer to query is YES) can be defined via a fourth parameter as an average inspiratory phase duration above a threshold, where the average is computed of the previous two respiratory cycles. In some examples, meeting the signal quality criteria (e.g. answer to query is YES) can be defined via various combinations of the respective first, second, third, and fourth parameters, including but not limited to, a combination of all four parameters. It will be understood that the sensor signal quality criteria and/or meeting the sensor signal quality criteria is not exclusively defined by the respective four parameters.

FIG. 15A is block diagram of a stimulation protocol element 490, according to one example of the present disclosure. In some examples, stimulation protocol element 490 includes at least some of substantially the same features and attributes as stimulation protocol element 450 as previously described in association with at least FIGS. 12-14, while further including at least the features shown in FIG. 15A.

As shown in FIG. 15A, stimulation protocol element 490 includes an override function 492 to take abrupt and sustained action to achieve a stable respiratory pattern. For instance, in some examples, persistent sleep disordered breathing is observed, which includes a series of unresolvable/intractable respiratory events (e.g. persistent apnea) that occur despite stimulation via either the independent stimulation function 454 or the respiratory-dependent function 456. In some examples, the override function 492 is activated when a stable respiratory pattern has not been detected for a predetermined period of time, such as 5 or 10 minutes. In some examples, the predetermined period of time is less than 5 minutes, such as when some number (e.g. 3 apneas) of apneas are detected prior to reaching 5 minutes.

Upon activation of the override function 492, therapy that was being implemented via the independent stimulation function 454 or via the respiratory-dependent function 456 is terminated or converted over to operation via a continuous stimulation function 494 (FIG. 15A) in which nerve stimulation is applied continuously (a 100% duty cycle) for a predetermined period of time. As previously described, in some examples, continuous stimulation refers to a train of stimulation pulses which occur in a relatively short time frame. For instance, in some examples, continuous stimulation corresponds to at least a finite number (e.g. 5, 10, etc.) of stimulation pulses per second. In some examples, continuous stimulation corresponds to at least 20 stimulation pulses per second. In some examples, continuous stimulation corresponds to at least 30 stimulation pulses per second. In some examples, the number of stimulation pulses per second is selectable by an operator via a control portion (e.g. 56 in FIG. 2C). In some examples, during such continuous stimulation, each stimulation pulse within a train of stimulation pulses includes a primary stimulation pulse followed by a separate recharge pulse, which is in turn followed by a non-stimulation phase before the next primary stimulation pulse.

In some examples, the override function 492 is implemented via an "other" function, in which nerve stimulation is applied that is not continuous but which has an intensity and duration substantially greater than implemented via the stimulation protocols of one of the independent stimulation function 454 (FIG. 12) or the respiratory-dependent function 456 (FIG. 12).

In some examples, operation via the override function 492 is maintained until at least one of a time limit, and/or the therapy manager detecting (via the sensed respiratory waveform) at least one respiratory cycle exhibiting an absence of sleep disordered breathing behavior as measured by a number of respiratory cycles and/or a severity threshold (in one example). In some examples, the time limit is 100 seconds, such as about 20 breaths. However, in some examples, the time limit can be much lower, such as 30 to 40 seconds. In some examples, the continuous stimulation is applied until detected sleep disordered breathing is absent for at least three consecutive respiratory cycles, i.e. a successful inspiration occurs for at least three consecutive respiratory cycles or some operator-selectable quantity (e.g. 2, 4) of consecutive respiratory cycles for a particular patient.

In some examples, the continuous stimulation is applied up to a predetermined maximum period. In some examples, the predetermined maximum period is at least 120 seconds. In some examples, the predetermined maximum period is selectable by an operator and can have values greater or less than 120 seconds, such as 130 seconds, 110 seconds, 90 seconds, etc. In general terms, the predetermined maximum period corresponds to an expired time by which fatigue of the stimulated muscle is complete or nearly complete.

In some examples, upon a determination that detected sleep disordered breathing behavior meets or exceeds the severity threshold, the therapy manager terminates operation in the respective independent and respiratory-dependent stimulation modes and initiates operation in a third mode including a stimulation protocol of a stimulation period and a non-stimulation period in a proportion of at least 3 to 1 wherein the stimulation period has a duration equal to or greater than a duration of at least four respiratory cycles.

In some examples, the duration of the stimulation period is about 30 seconds and the duration of the non-stimulation period is about 10 seconds. In some examples, the duration of the stimulation period is about 30 seconds and the duration of the non-stimulation period is about 5 seconds.

Upon determination that a stable respiratory period has been established, operation in the override function 492 terminates and operation is resumed via the independent stimulation function 454 (FIG. 12) consistent with the functionality previously described in association with at least FIGS. 12-14.

FIG. 15B is a diagram 500 schematically illustrating aspects of selecting a stimulation protocol 501, according to one example of the present disclosure. In some examples, at least some aspects of selecting a stimulation protocol as expressed in diagram 500 can be embodied as a method while in some examples, at least some aspects of selecting a stimulation protocol as expressed in diagram 500 can be embodied as operational aspects of a stimulation protocol management associated with a therapy manager 16 as described in association with at least FIGS. 1-15A.

As shown at 502, respiratory information can be periodically sensed during a treatment period and without synchronization to stimulation. In other words, in at least some instances, this periodic sensing is not related to and/or does not result in synchronizing stimulation to sensed respiratory information. Rather, such periodic sensing can be used to enhance and/or evaluate the effectiveness of the stimulation, among other uses for such periodically sensed respiratory information.

As shown at 504 in FIG. 15B, if the duration of the sensed respiratory cycles (among a sample of respiratory cycles) is less variable from cycle-to-cycle than a duration variability criteria, then a stimulation protocol is adopted in which a repeating stimulation cycle is applied and which has a duration different than a duration of the reference respiratory cycle for this patient. This arrangement introduces an intentional stagger or offset between the duration of the stimulation cycle and the duration of respiratory cycle, which may ensure overlap of at least some stimulation periods (of the stimulation cycles) with the actual inspiratory phases of the respiratory cycles of the patient a majority of the time.

In some examples, the duration variability criteria establishes a measure of the variability of a duration of sensed respiratory cycles. The variability can be measured by a frequency of changes in the duration during an observation period and/or a magnitude of change in such durations during the observation period. Further details regarding the observation period are identified below.

In some examples, the duration variability criteria is based on several factors, including but not limited to, a duration of a typical stable respiratory period (e.g. 3-6 seconds, depending on the patient), the minimum duration of an apnea (e.g. 10 seconds), and/or an observation period (e.g. 5 minutes) following a change in stimulation parameters. In some examples, the observation period can more than 5 minutes while in some examples, the observation period can be less than 5 minutes, such as when some number (e.g. 3 apneas) of apneas are detected prior to reaching 5 minutes. In some examples, the duration variability criteria is further based on a standard deviation of respiratory periods of less than 1 second and a sample period of at least 4 minutes.

With further reference to 504 in FIG. 15B, in some examples, this arrangement is implemented via stimulation protocol 210 in FIG. 3B in which a respiratory waveform is represented via a series 202 of respiratory cycles 204A-204H. Moreover, in this example, the duration of the stimulation cycle (4 stimulation periods plus 1 non-stimulation period) is less than a duration (R) of the reference respiratory cycles, such that the repeating stimulation cycle has a duration different than a duration (R) of the reference respiratory cycle.

This arrangement ensures that no matter when the stimulation protocol is generally activated, no more than a finite number (e.g. 2, 3, 4) of respiratory cycles would occur without a stimulation period significantly coinciding with an inspiratory phase 162 of the respective respiratory phases. This phenomenon occurs, at least in part, because of a sufficiently large difference between the duration of the stimulation cycle and the duration of the respiratory cycle, and in view of the relative proportion of the stimulation period to the non-stimulation period.

In some examples, other example stimulation protocols are used for implementation. For instance, example stimulation protocols 220, 230 as described in association with at least FIGS. 3C, 3D can be used. It is noted that stimulation protocols 220, 230 include stimulation cycles having a duration greater than a duration (R) of the reference respiratory cycle as shown in the respective legends 229, 239 of FIGS. 3C, 3D, respectively.

As shown at 506 in FIG. 15B, if the duration of the sensed respiratory cycle (of a sensed sample of respiratory cycles) is more variable than the duration variability criteria noted above, then a repeating stimulation cycle is applied and which has a duration generally matching a duration of a reference respiratory cycle. In this instance, the natural variability of the duration of the patient's respiratory cycle can be used to introduce a stagger or offset relative to the duration of the stimulation cycle, which may ensure an overlap of at least some stimulation periods relative to at least some of the inspiratory phases of the patient's live respiratory cycles at least a majority of the time.

In some examples, the reference respiratory cycle is defined by a patient-specific average respiratory cycle obtained at an earlier point in time. In some examples, the reference respiratory cycle is defined by a multi-patient specific average respiratory cycle obtained from a database.

In some examples, this arrangement is implemented via stimulation protocol 240 in FIG. 3E in which a respiratory waveform is represented via a series 244 of respiratory cycles 245A-245M. Accordingly, FIG. 3E models the situation in which the duration (R1) of the respiratory cycles has varied (relative to the duration R of its base/stable respiratory cycle) by more than a threshold. In some examples, the threshold includes R changing (increasing or decreasing) in duration by 5 percent. In this instance the duration R1 represents about an 8 percent change from the duration R because the respiratory cycles 245A-245M have a duration R1 of 6½ time units whereas duration R is equal to 6 time units. It will be understood, of course, that other numeric values that are more or less than 5 percent can be used as the threshold.

While FIG. 3E exhibits a duration R1 which remains constant at least for the illustrated series of respiratory cycles, it will be understood that duration R1 may have a different value (e.g. longer or shorter) in subsequent respiratory cycles and/or that duration R1 may have had different values (e.g. longer or shorter) in preceding respiratory cycles. Accordingly, at least with respect to the method of FIG. 15B, duration R1 should not be viewed as being indefinitely static, but rather as having a particular value at one snapshot in time.

It will be further understood that variations in the duration of the respiratory cycle may be exhibited as decreases (instead of increases) and that variations in the duration of the respiratory cycle are not permanent but may last some finite number of respiratory cycles before reverting to a baseline or changing to yet another non-R duration.

In the example of FIG. 3E, the duration of the stimulation cycle (4 stimulation periods plus 2 non-stimulation periods) is less than a duration (R1) of the respiratory cycles but with the duration of the stimulation cycles being equal to the duration (R) of the reference respiratory cycle (which is based on a historical baseline in at least some examples).

With this arrangement, because the duration (R1) of the sampled respiratory cycle (obtained via periodic sensing) has varied relative to a reference duration R, the therapy manager 16 utilizes a stimulation cycle having a duration to match the duration of the reference respiratory cycle, which in turn introduces the above-mentioned intentional stagger or offset.

This arrangement ensures that no matter when the stimulation protocol is generally activated, no more than a finite number of respiratory cycles would occur without a stimulation period significantly coinciding with an inspiratory phase of the respective respiratory phases. This phenomenon occurs, at least in part, because of a sufficiently large difference between the duration of the stimulation cycle and the duration of the respiratory cycle, and in view of the relative proportion of the stimulation period to the non-stimulation period.

Accordingly, as represented at block 506, when the duration of the periodically sensed respiratory cycle varies more than a duration variability criteria, the therapy manager ensures an appropriate level of stimulation coinciding with the inspiratory phases of the respiratory cycles by intentionally not adjusting the duration of the stimulation cycle to match the modified duration R1 exhibited by the periodically sensed respiratory cycles.

While FIG. 3E exhibits a duration R1 which remains constant at least for the illustrated series of respiratory cycles, it will be understood that duration R1 may have a different value (e.g. longer or shorter) in subsequent respiratory cycles and/or that duration R1 may have had different values (e.g. longer or shorter) in at least some preceding respiratory cycles. Accordingly, at least with respect to the method of FIG. 15B, duration R1 should not be viewed as being indefinitely static, but rather as having a particular value at one snapshot in time.

FIG. 15C is a block diagram schematically illustrating a stimulation protocol selector element 520, according to one example of the present disclosure. In some examples, the stimulation protocol selector element 520 includes, and enables, selection between a first function 522 and a second function 524. In some examples, a selection via element 520 between first function 520 and second function 522 can be implemented in association with the aspects of block 502 in FIG. 15B. In some examples, first function 520 can be implemented via at least some of the aspects of stimulation selection as described in association with block 504 in FIG. 15B while second function 522 can be implemented via at least some of the aspects of stimulation selection as described in association with block 506 in FIG. 15B.

Figure 15D:
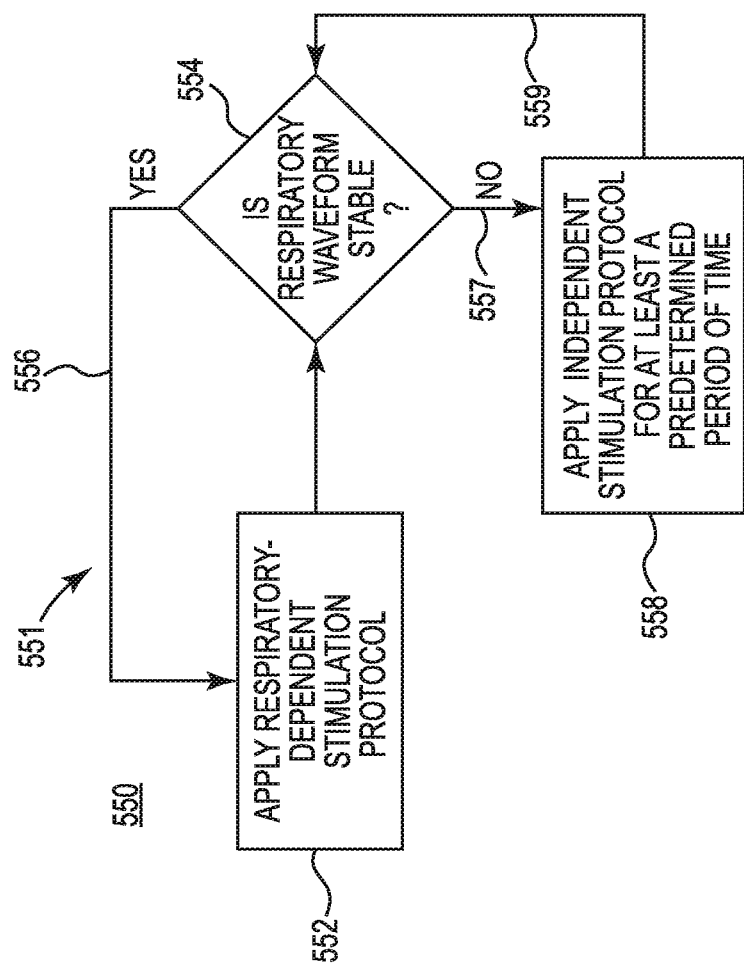
FIG. 15D is a diagram schematically illustrating at least some aspects of stimulation protocol selection, according to one example of the present disclosure.

FIG. 15D is a diagram 550 schematically illustrating a relationship between, and automatically selection between, the independent stimulation protocol 454 (FIG. 12) and the respiration-dependent stimulation protocol 456 (FIG. 12), according to one example of the present disclosure. In some examples, at least some aspects of stimulation protocol selection 551 in diagram 550 can be embodied as a method while in some examples, at least some aspects of stimulation protocol selection in diagram 550 can be embodied as operational aspects of a stimulation protocol manager of a therapy manager, as described in association with at least FIGS. 11B-13.

In some examples, operation of the at least partially implantable stimulation system is implemented via providing cooperation or complementary deployment of the respective stimulation protocols 454, 456 (at least FIGS. 11B-13). Accordingly, as shown at 552 in FIG. 15D, operation starts in a respiratory-dependent stimulation protocol.

With further reference to FIG. 15D, based on monitoring of the sensed respiratory waveform, at repeating intervals, at 554 it is queried whether the respiratory waveform is sufficiently stable to support continued operation of respiratory-dependent stimulation at 552. If the answer to the query at 554 is YES, then pathway 556 affirms continued operation of respiratory-dependent stimulation at 552. However, if the answer to the query at 554 is NO, then pathway 557 directs initiation of operation of independent stimulation at 558 of FIG. 15D for at least a predetermined period of time. The first predetermined period of time is defined in substantially the same manner as previously described in association with at least FIG. 14, and the operation of the independent stimulation function at 558 is not a test mode. Rather, the independent stimulation (at 558) operates for at least the predetermined period of time to apply therapeutic stimulation to achieve a stable respiratory behavior and a stable respiratory waveform.

Upon operation of independent stimulation at 558 for at least the predetermined period of time, the query at 554 is periodically implemented via pathway 559. If the answer to the query (at 554) is YES, then operation in independent stimulation at 558 in FIG. 15D is terminated as operation is returned via pathway 556 to respiratory-dependent stimulation at 552 in FIG. 15D. For at least the current example, it will be understood that, in the event that no stable respiratory waveform is established, the operation would remain in the independent stimulation at 558 without reverting operation into respiratory-dependent stimulation at 552.

In some examples, the query at 554 is performed by monitoring parameters indicative of respiratory signal sensing quality (i.e. sensor signal quality criteria), such as but not limited to, peak to peak amplitude, inspiratory duty cycle, respiratory rate, etc.

FIG. 16A is diagram 640 schematically illustrating a nerve stimulation protocol 641, according to one example of the present disclosure.

In one aspect, diagram 640 omits a representative respiratory waveform relative to the stimulation protocol because, in at least some examples, operation according to independent stimulation function 14 (FIG. 1A) occurs regardless of whether a sensed respiratory waveform is available or reasonably stable. Accordingly, diagram 640 illustrates stimulation periods relative to predetermined time periods instead of relative to inspiratory and expiratory phases of a normal respiratory pattern, as further described and illustrated below.

As shown in FIG. 16A, a nerve stimulation protocol 641 comprises stimulation segments 642 and non-stimulation segments 648, 649 (i.e. rest periods), which may occur within a time frame (T). In this arrangement, the time frame T comprises a series of eight time units with each time unit having a duration t, as shown in FIG. 16A. In some examples, a combination of two consecutive time units have a duration R that generally corresponds to a duration of a respiratory cycle. In one aspect, the duration of one time unit (t) comprises one-half of duration R.

As shown in diagram 640, stimulation protocol 641 includes a repeating sequence of continuous stimulation segments 642 and non-stimulation segments 648, 649. Each stimulation segment 642 has a duration of 3 time units (t), each non-stimulation segment 648 has a duration of two time units, and each non-stimulation segment 649 has a duration of one time unit. This pattern is represented by legend 645 as 3:SK2:3:SK1, where SK represents "skip" to indicate skipping stimulation.

As further shown by diagram 640, as this stimulation cycle pattern (3:SK 2:3:SK 1) is repeated through a series of time frames T (with each time frame T including 8 time units), one can identify the number of stimulation time units that occurs within each time frame T. For example, the first time frame includes 6 stimulation time units out of 8 total time units, followed by three time frames T including 5 stimulation time units out of 8 total time units, followed by two "six stimulation time unit" time frames T, and then three "five stimulation time unit" time frames T. With this in mind, one can express a pattern of the stimulation time units for the first twelve consecutive time frames as 6:5:5:5:6:6:5:5:5.

Via the stimulation protocol 641, a therapeutic nerve stimulation regimen is applied in which no period of four consecutive respiratory cycles will transpire without a stimulation period coinciding with an expected inspiratory phase of a respiratory cycle. In this stimulation protocol, the duration of stimulation periods exceeds the duration of non-stimulation periods.

Figure 16B:
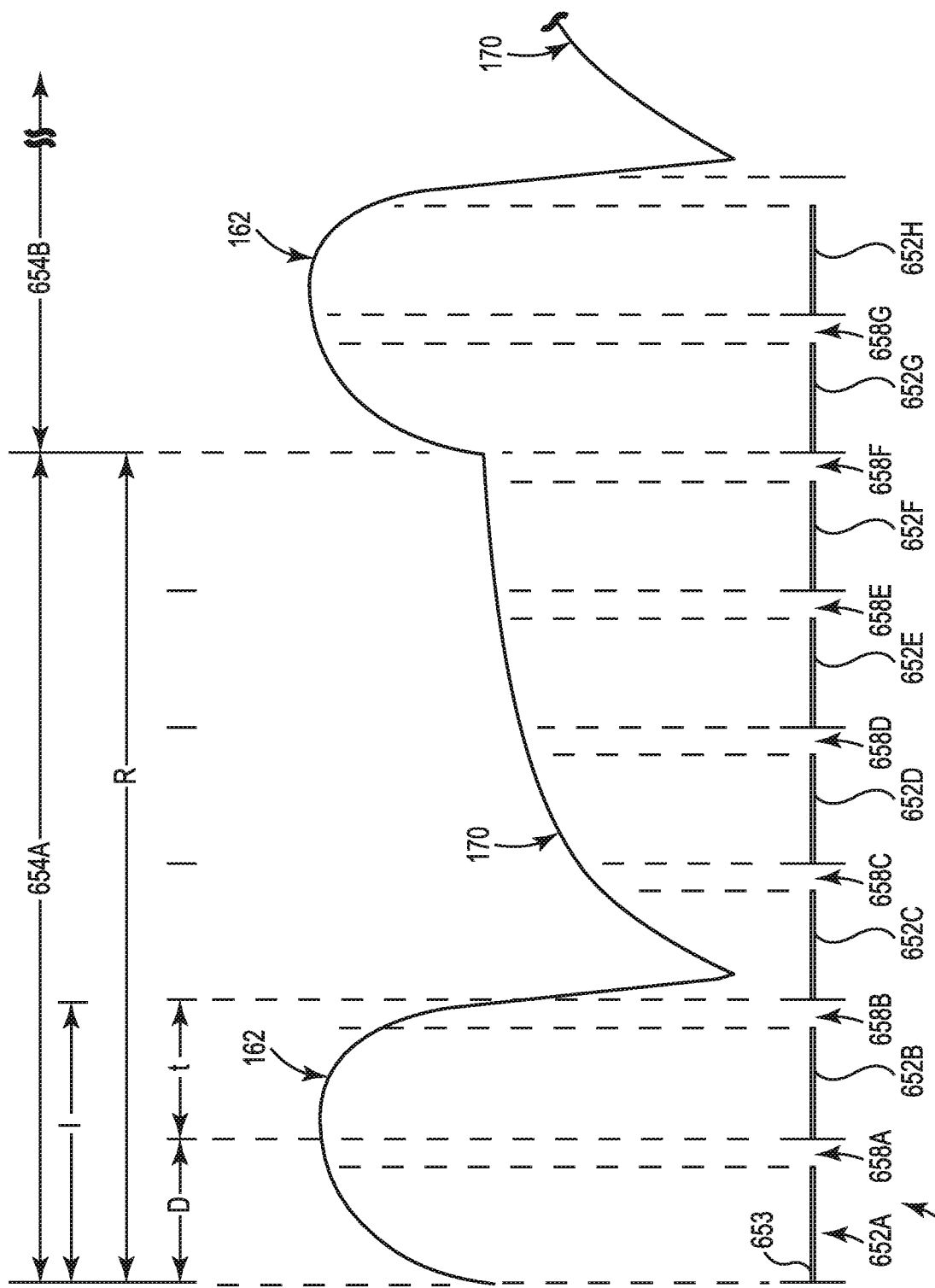
FIG. 16B is a diagram schematically illustrating a stimulation protocol, according to one example of the present disclosure.

FIG. 16B is a diagram 651 schematically illustrating a stimulation protocol 650, according to one example of the present disclosure. In some examples, protocol 650 exhibits at least some of substantially the same features and attributes as the stimulation protocols, as previously described in association with at least FIGS. 3B-3E. In general terms, via stimulation protocol 650, via stimulation element 12 (FIG. 1A) and/or therapy manager 16 (FIG. 1B) the independent stimulation function 14 implements asynchronous nerve stimulation which to promote stable respiration despite potential sleep disordered breathing.

As illustrated in FIG. 16B, the stimulation protocol 650 operates according to stimulation cycles in which the duration (D) of each stimulation cycle is less than the duration (R) of the reference respiratory cycles 654A, 654B. Moreover, in some examples, the stimulation cycle has a duration (D) which is significantly less (at least half or less) than the duration (R) of the reference respiratory cycles 654A, 654B. In one of these examples, a duration (D) of the stimulation cycle is less than 30 percent of the duration (R) of the reference respiratory cycles 654A, 654B. In one of these examples, a duration (D) of the stimulation cycle is less than 20 percent of the duration (R) of the reference respiratory cycle 654A, 654B. In one such instance, as illustrated in FIG. 16B, the duration (D) of the stimulation cycle is about 1 second, whereas the duration (R) of the reference respiratory cycle is about 6 seconds.

In some examples of implementing stimulation protocol 650, within a given stimulation cycle the stimulation period (e.g. 652A, 652B, etc.) and the non-stimulation period (e.g. 658A, 658B, etc.) are in a proportion of 4 to 1 to yield a stimulation duty cycle of 80 percent (for each stimulation cycle). In such examples, each stimulation cycle lasts about 1 time unit (t), including a continuous stimulation period of 4"⅕" time units followed by a non-stimulation period of a single "⅕" time unit, with this stimulation cycle being repeated continuously when nerve stimulation via stimulation protocol 650 is implemented. Accordingly, in some examples, the duration of the entire stimulation cycle (e.g. 4"⅕" time units of stimulation and a single "⅕" time unit of non-stimulation) is 1 time unit (t), which is significantly less than the duration R of the respiratory cycle, which is 6 time units in this example.

However, it will be understood that in some examples, the duration of the stimulation period need not coincide with a discrete number (e.g. 4) of fractional time units (e.g. "⅕" time units) and the duration of the non-stimulation period need not coincide with a discrete number (e.g. 1) of fractional time units (e.g. "⅕" time units).

In some examples, the duration (R) of the reference respiratory cycles (e.g. 654A, 654B, etc.) can be selected to be more or less than 6 time units (t), as shown in FIG. 16B. In some examples, the duration (D) of each stimulation cycle (including a stimulation period, such as 652A and a non-stimulation period, such as 658A) can be selected to be more or less than one time unit (t).

In FIG. 16B, the first end 653 of stimulation period 652A is shown as coinciding with the beginning of an inspiratory phase 162 of the respiratory cycle 654A. However, it will be understood that the beginning 653 of the stimulation period 652A is not synchronized relative to the inspiratory phase 162. Rather, the beginning 653 of stimulation period 652A is shown as coinciding with the beginning of inspiratory phase 162 for illustrative simplicity in juxtaposing the stimulation protocol 650 relative to the reference respiratory cycles 654A, 654B, etc. Accordingly, it will be understood that when stimulation (according to stimulation protocol 650) is initiated during a treatment period, the beginning of the stimulation period 652A may coincide with a different portion of the reference respiratory cycle (e.g. 654A) than shown in FIG. 16B.

As further shown in FIG. 16B, in one aspect, each respective non-stimulation period (e.g. 658A, 658B, etc.) has a duration significantly less than (e.g. at least less than half) a duration of each respective stimulation period (e.g. 652A, 652B, etc.). In one aspect, the duration of each stimulation period (e.g. 652A, 652B, etc.) is also significantly less than (e.g. at least less than 30%) a duration (R) of the respective reference respiratory cycles (e.g. 654A, 654B, etc.). In some examples, in stimulation protocol 650, the duration (D) of each stimulation period (e.g. 652A, 652B, etc.) is significantly less than a duration (I) of the inspiratory phase 162 of an individual respiratory cycle (e.g.

654A) such that multiple, different stimulation periods occur during a single inspiratory phase 162. Accordingly, with this arrangement, several stimulation cycles will be repeated within a single reference respiratory cycle.

In some examples, the relatively short duration of the stimulation cycle causes a successive stimulation period (e.g. 652B) to begin at a different place within the inspiratory phase 162 of the reference respiratory cycle than prior stimulation period (e.g. 652A), such that the stimulation pattern is considered to be independent of (i.e. not synchronized relative to) the characteristics of the respiratory cycle. Rather, the asynchronous nature of stimulation protocol 650 is further exhibited via the stimulation periods 652C-652F occurring during the expiratory phase 170 of respiratory cycle 654A because the same stimulation cycle is repeated regardless of where the stimulation periods falls relative to different portions of the reference respiratory cycle.

Accordingly, even though the stimulation is not synchronized relative to a characteristic (e.g. inspiration) of the respiratory waveform, no matter where the stimulation protocol 650 is started relative to a series of respiratory cycles, the short duration (D) of the stimulation cycle (relative to the longer duration R of the respiratory cycle) ensures that at least a portion of two stimulation periods (e.g. 652A, 652B) will significantly overlap (at least a majority) the inspiratory phase 162 of the respective reference respiratory cycles throughout the portion of the treatment period during which stimulation protocol 650 is applied.

In some examples, via therapy manager 16 (FIG. 1B) a clinician can set a criteria how many respiratory cycles through which the stimulation protocol 650 will be applied before stimulation terminates and/or before a different stimulation protocol is implemented. In some examples, the criteria are based on a predetermined amount of time and/or a predetermined number of respiratory cycles for a particular patient.

It will be understood that each inspiratory phase 162 of each respiratory cycle (204A-204H) is shown in its ideal form in FIG. 3B, and that in some instances where the inspiratory phase 162 at least partially coincides with one of the respective non-stimulation periods (e.g. 218D), the inspiratory phase may sometimes have an irregular shape compared to the idealized shape shown in FIG. 3B.

Accordingly, via stimulation protocol 650, the independent stimulation function 14 of therapy manager 16 (FIG. 1B) employs asynchronous nerve stimulation to achieve stable respiration despite potential sleep disordered breathing.

In some examples, the stimulation protocol 650 (and similar protocols described above) is implemented via the "other" function 496 (FIG. 15A) of override function 492 to help overcome the type of persistent sleep-disordered breathing that does not become controlled via less intensive stimulation protocols. Accordingly, stimulation protocol 650 provides stimulation, which is not continuous but which has an intensity substantially greater than implemented via the stimulation protocols of one of the independent stimulation function 454 (FIG. 12) or the respiratory-dependent function 456 (FIG. 12), as previously illustrated in association with at least FIGS. 3B-3E.

However, unlike a continuous stimulation pattern such as provided via continuous function 494 (FIG. 15A) of override function 492, stimulation protocol 650 regularly provides non-stimulation periods to enable the targeted nerve and/or muscle to rest somewhat among the stimulation periods, while still achieving an overall 80% stimulation duty cycle. In this arrangement, multiple stimulation periods can occur during each inspiratory phase of the repeating reference respiratory cycles such that no inspiratory phase occurs without stimulation occurring during at least a majority of any given inspiratory phase. In one aspect, such an arrangement may contribute to more favorable patient comfort or tolerance for the implementation of the "other" override function and/or contribute to diminishing any potential nerve or muscle fatigue.

In some examples, variations of stimulation protocol 650 are implemented in which the duration (D) of the stimulation cycle is significantly less than the duration (R) of the reference respiratory cycle, and the stimulation duty cycle is about 60 percent or 70 percent (instead of 80 percent). In such an arrangement, multiple stimulation periods can still occur during each inspiratory phase of the repeating reference respiratory cycles such that no inspiratory phase occurs without stimulation occurring during at least a majority of any given inspiratory phase, but with more non-stimulation available. In one aspect, such an arrangement may provide more comfort for some patients and/or potentially less muscle fatigue, as compared to the illustrated example stimulation protocol 650 having an 80% stimulation duty cycle (with relatively short duration stimulation cycles).

As with the other example stimulation protocols described herein, stimulation protocol 650 can be modified by an operator via the various parameters, functions, and components as previously described in association with at least FIGS. 4-5 can be selected and/or adjusted via a control portion (56 in FIG. 2C; 360 in FIG. 9; 380 in FIG. 10) in association with user interface (396 in FIG. 11A; 400 in FIG. 11B).

Figure 17A:
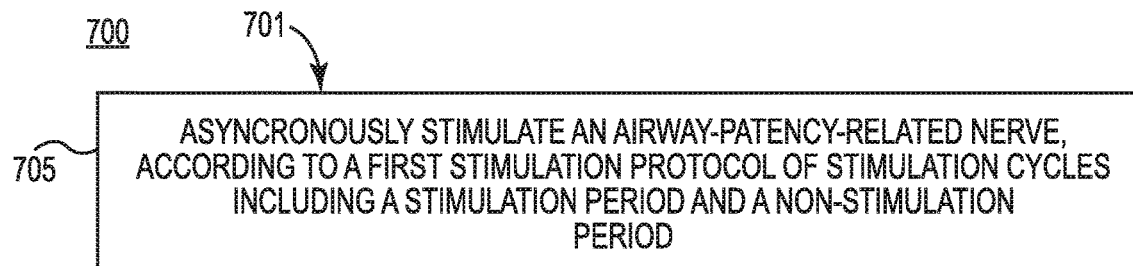
FIG. 17A is a flow diagram schematically illustrating a method of nerve stimulation, according to one example of the present disclosure.

FIG. 17A is a flow diagram 700 of a method 701 of nerve stimulation to treat sleep disordered breathing, according to one example of the present disclosure. In some examples, method 701 is performed using the components, elements, systems, etc. previously described and illustrated in association with FIGS. 1-16B. In some examples, method 701 is performed using components, elements, systems, etc. other than those previously described and illustrated in association with FIGS. 1-16B.

As shown in FIG. 17A, at 705 method 701 includes asynchronously stimulating an airway-patency-related nerve, according to a first stimulation protocol of stimulation cycles including a stimulation period and a non-stimulation period.

Figure 17B:
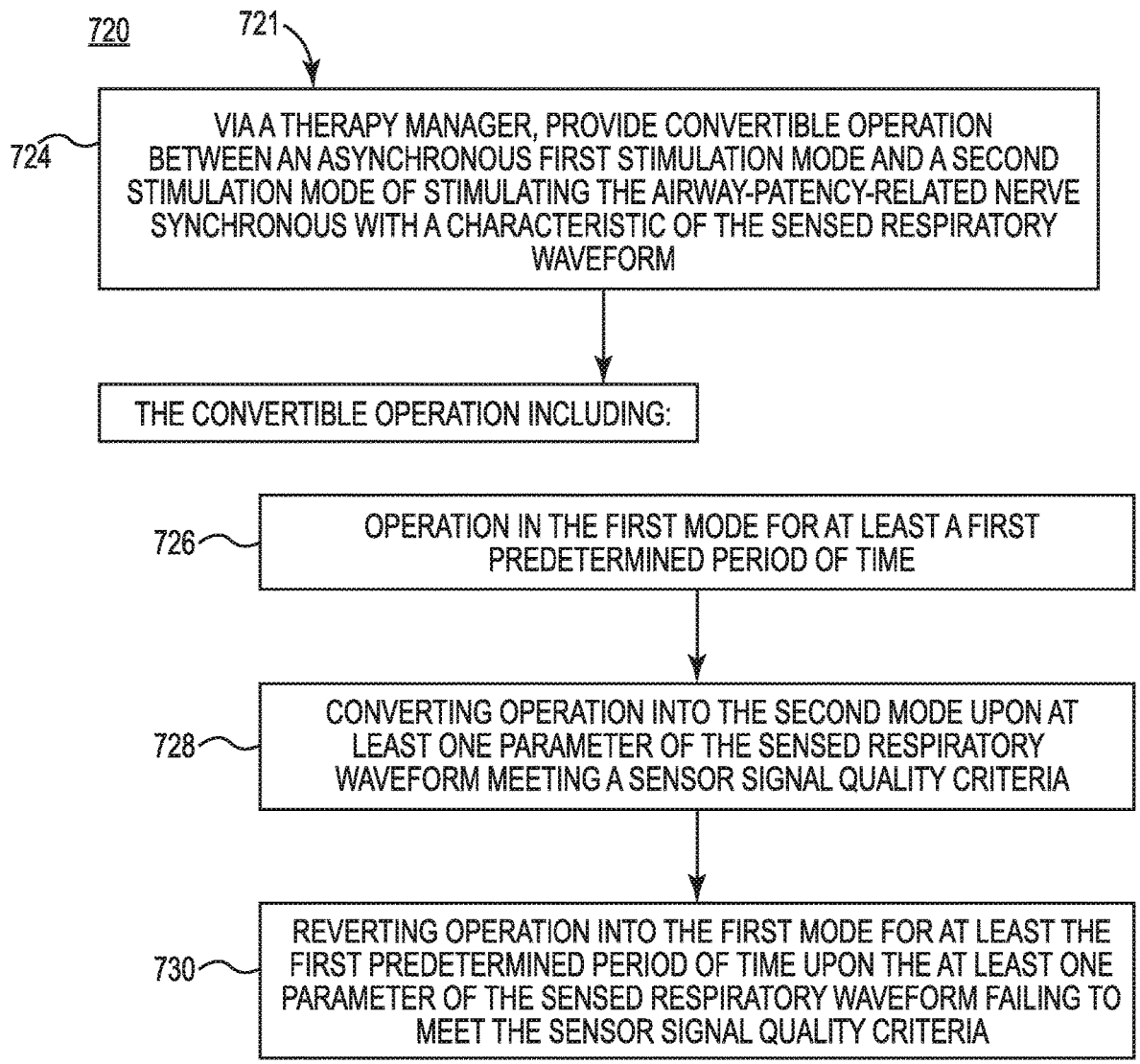
FIG. 17B is a flow diagram schematically illustrating a method of nerve stimulation, according to one example of the present disclosure.

FIG. 17B is a flow diagram 720 of a method 721 of nerve stimulation to treat sleep disordered breathing, according to one example of the present disclosure. In some examples, method 721 is performed using the components, elements, systems, etc. previously described and illustrated in association with FIGS. 1-16B. In some examples, method 721 is performed using components, elements, systems, etc. other than those previously described and illustrated in association with FIGS. 1-16B.

As shown in FIG. 17B, in cooperation with the method 701 of FIG. 17A, method 721 includes performing nerve stimulation via the therapy manager providing automatic convertible operation between the independent stimulation mode/function of FIG. 17A and a second stimulation mode of stimulating the airway-patency-related nerve synchronous with a characteristic of the sensed respiratory waveform, as shown at 724. With this arrangement, the therapy manager causes operation in the first mode for at least a first predetermined period of time (726) and converts operation into the second mode upon at least one parameter of the sensed respiratory waveform meeting a sensor signal quality criteria (728). Upon the at least one parameter of the sensed respiratory waveform failing to meet the sensor signal quality criteria (730), operation reverts into the first mode for at least the first predetermined period of time In this example, the first mode acts as the default mode of operation.

In some examples, the sensor signal quality criteria is indicative of the system's ability to actually deliver stimulation at the targeted portion of the respiratory period with a high degree of confidence. In some examples the system may define an obstructive event (e.g. apnea/hypopnea) as lasting at least 10 seconds, then the above-mentioned high degree of confidence would correspond to not missing the target portion of the respiratory period twice in consecutive respiratory cycles.

In some examples, the sensor signal quality criteria can be indicative of a patient's real-time condition either in the absence of or in the presence of stimulation. In some examples, the sensor signal quality criteria can be indicative of sensor noise, thereby indicating how well the sensor signal correlates with the patient's real-time condition.

Figure 17C:
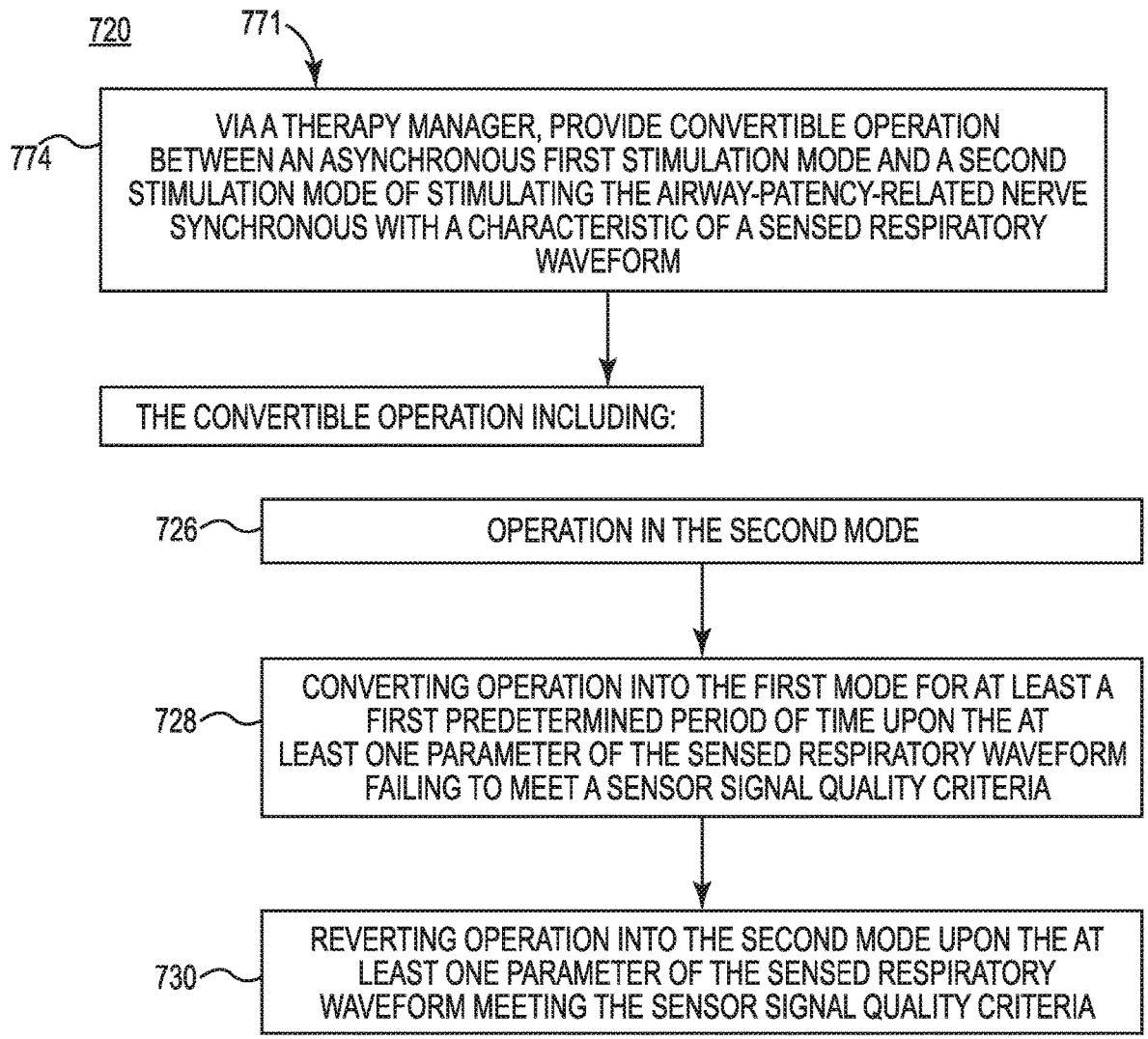
FIG. 17C is a flow diagram schematically illustrating a method of nerve stimulation, according to one example of the present disclosure.

However, in some examples, the second mode can act as the default mode of operation. Accordingly, as shown in FIG. 17C, in cooperation with the method 701 of FIG. 17A, method 771 includes performing nerve stimulation via the therapy manager providing convertible operation between the independent stimulation mode/function of FIG. 17A and a second stimulation mode of stimulating the airway-patency-related nerve synchronous with a characteristic of the sensed respiratory waveform, as shown at 774. With this arrangement, the therapy manager causes operation in the second mode (776), and upon at least one parameter of the sensed respiratory waveform failing to meet a sensor signal quality criteria, operation converts into the first mode for at least a first predetermined period of time (778). At 780, upon the at least one parameter of the sensed respiratory waveform meeting the sensor signal quality criteria, operation reverts back into the second mode.

In some examples, with respect to at least FIGS. 17B and 17C, the conversion between the first stimulation mode and the second stimulation mode is automatic.

Figures 18, 19:
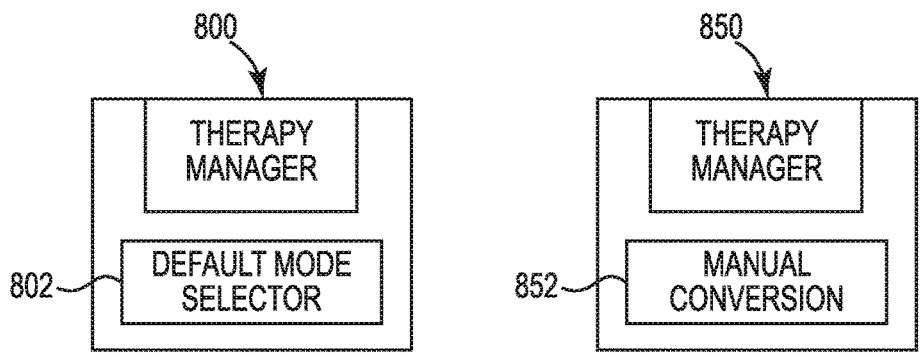
FIG. 18 is a block diagram schematically illustrating a therapy manager, according to one example of the present disclosure.
FIG. 19 is a block diagram schematically illustrating a therapy manager, according to one example of the present disclosure.

With respect to selection of the first mode or the second mode in association with FIGS. 17B and 17C, in some examples a therapy manager 800 includes a default mode selector function 802 (as shown in FIG. 18) to enable user selection of either the first mode or the second mode as a default mode. In some examples, the therapy manager 800 also comprises at least some of the features and attributes as therapy manager 16 (FIG. 1B) and other examples of a therapy manager, as previously described in association with at least FIGS. 1-17C.

With respect to selection of the first mode or the second mode in association with FIGS. 17B and 17C, in some examples a therapy manager 850 includes a manual conversion function 852 (as shown in FIG. 19) to selectively cause conversion between the two different stimulation modes. In one aspect, such selective conversion can be implemented during operator titration of the therapeutic treatment as the operator adjusts parameters of the stimulation protocols for a particular patient. In some examples, the therapy manager 850 also comprises at least some of the features and attributes as therapy manager 16 (FIG. 1B) and other examples of a therapy manager, as previously described in association with at least FIGS. 1-17C. Accordingly, at least some examples of the present disclosure provide for a robust scheme to increase the effectiveness of nerve stimulation to treat sleep disordered breathing.

Although specific examples have been illustrated and described herein, it will be appreciated by those of ordinary skill in the art that a variety of alternate and/or equivalent implementations may be substituted for the specific examples shown and described without departing from the scope of the present disclosure. This application is intended to cover any adaptations or variations of the specific examples discussed herein.

What is claimed is:

1. A device for treating obstructive sleep apnea, comprising:
    a non-cardiac stimulation element to engage and to stimulate an upper-airway-patency-related nerve, according to a first stimulation therapy protocol not synchronized relative to actively-sensed respiratory information, wherein the first stimulation therapy protocol comprises a series of repeating stimulation cycles in which each stimulation cycle includes a stimulation period and a non-stimulation period,
    wherein each stimulation period includes continuous stimulation and has a minimum duration equal to or greater than an inspiratory reference of a reference respiratory cycle, wherein the inspiratory reference corresponds to a duration of an inspiratory phase of the reference respiratory cycle, and wherein the reference respiratory cycle comprises at least one of:
        a historical patient-specific average respiratory cycle for stable respiration; and
        a multi-patient average respiratory cycle for stable respiration, and
    wherein each stimulation period of each respective stimulation cycle has a duration greater than a duration of the inspiratory reference of the reference respiratory cycle and the stimulation period is followed by the non-stimulation period of the respective stimulation cycle comprising a duration less than the duration of the stimulation period.

2. The device of claim 1, wherein the non-cardiac stimulation element comprises an implantable electrode and a pulse generator electrically connected to the implantable electrode.

3. The device of claim 2,
    wherein the implantable electrode comprises a cuff electrode including at least one operative contact group through which the stimulation is deliverable non-selectively to the upper-airway-patency-related nerve.

4. The device of claim 1, wherein a total duration of stimulation via the first stimulation protocol during a treatment period is greater than 30 percent of the total duration of the treatment period.

5. The device of claim 1, wherein the duration of the stimulation period comprises
    at least 50 percent of a duration of the stimulation cycle.

6. The device of claim 1, wherein the duration of the stimulation period comprises
    at least 50 percent of a duration of the reference respiratory cycle.

7. The device of claim 1, wherein the duration of each respective stimulation cycle is less than the duration of the reference respiratory cycle, and a duration of the stimulation period exceeds the duration of the non-stimulation period by a factor of at least 3.

8. The device of claim 1, wherein the duration of each respective stimulation cycle is greater than the duration of the reference respiratory cycle.

9. The device of claim 8, wherein the stimulation period and the non-stimulation period are in a proportion of at least 1.5 to 1.

10. The device of claim 8, wherein the duration of the stimulation cycle is less than a duration of two consecutive reference respiratory cycles.

11. The device of claim 1, wherein the duration of each respective stimulation cycle is equal to the duration of the reference respiratory cycle, and wherein the duration of the reference respiratory cycle differs from a duration of a real time respiratory cycle from actively-sensed respiration information by an amount exceeding a duration variability criteria.

12. The device of claim 1, comprising:
a processor; and
a non-volatile computer readable medium storing instructions, executable on the processor, to implement the non-cardiac stimulation element and to perform the first stimulation therapy protocol.

13. The device of claim 1, comprising:
a sensing element to at least periodically actively sense respiratory information to obtain the actively-sensed respiratory information unrelated to stimulation synchronization,
wherein the non-cardiac stimulation element is activated for stimulation upon the sensing element identifying, via at least the actively-sensed respiratory information, obstructive sleep apnea behavior which meets or exceeds a severity threshold and wherein the non-cardiac stimulation element is deactivated upon the sensing element identifying, via at least the actively-sensed respiratory information, that the obstructive sleep apnea behavior is less than the severity threshold.

14. The device of claim 1, comprising:
a sensing element to obtain the actively-sensed respiratory information; and
a control portion including:
a processor; and
a non-volatile memory storing instructions, executable via the processor, to:
provide convertible operation via a therapy manager between:
a first stimulation mode implementing the first stimulation therapy protocol; and
a second stimulation mode of stimulating the upper-airway-patency-related nerve synchronous with a characteristic of the actively-sensed respiratory information.

15. The device of claim 1, wherein the stimulation period and the non-stimulation period are in a proportion of at least 1.5 to 1.

* * * * *